US011053286B2

(12) United States Patent
Kotecha et al.

(10) Patent No.: US 11,053,286 B2
(45) Date of Patent: Jul. 6, 2021

(54) STABILISED FMDV CAPSIDS

(71) Applicant: The Pirbright Institute, Woking (GB)

(72) Inventors: Abhay Kotecha, Oxford (GB); David Stuart, Oxford (GB); Elizabeth Fry, Oxford (GB); Robert Esnouf, Oxford (GB)

(73) Assignee: The Pirbright Institute, Pirbright (GB)

( * ) Notice: Subject to any disclaimer, the term of this patent is extended or adjusted under 35 U.S.C. 154(b) by 5 days.

(21) Appl. No.: 16/250,207

(22) Filed: Jan. 17, 2019

(65) Prior Publication Data

US 2019/0135874 A1  May 9, 2019

Related U.S. Application Data

(62) Division of application No. 14/779,797, filed as application No. PCT/EP2014/055904 on Mar. 25, 2014, now Pat. No. 10,294,277.

(30) Foreign Application Priority Data

Mar. 26, 2013 (EP) ..................................... 13161139

(51) Int. Cl.
| | |
|---|---|
| *A61K 39/125* | (2006.01) |
| *C12N 7/00* | (2006.01) |
| *C07K 14/005* | (2006.01) |
| *A61K 39/12* | (2006.01) |
| *A61K 39/135* | (2006.01) |
| *A61K 39/00* | (2006.01) |

(52) U.S. Cl.
CPC ............ *C07K 14/005* (2013.01); *A61K 39/12* (2013.01); *A61K 39/135* (2013.01); *C12N 7/00* (2013.01); *A61K 2039/5258* (2013.01); *A61K 2039/552* (2013.01); *C12N 2770/32122* (2013.01); *C12N 2770/32123* (2013.01); *C12N 2770/32134* (2013.01); *C12N 2770/32151* (2013.01)

(58) Field of Classification Search
None
See application file for complete search history.

(56) References Cited

U.S. PATENT DOCUMENTS

| | | | |
|---|---|---|---|
| 7,531,182 B2 | 5/2009 | King et al. | |
| 9,109,014 B2 * | 8/2015 | Weiner | .................. A61N 1/327 |
| 9,145,548 B2 | 9/2015 | Fowler et al. | |
| 2004/0001864 A1 | 1/2004 | King et al. | |
| 2011/0236416 A1 | 9/2011 | Audonnet et al. | |

FOREIGN PATENT DOCUMENTS

| | | |
|---|---|---|
| CN | 1440296 A | 10/2016 |
| RU | 2467014 C2 | 11/2012 |
| WO | 2002000251 A1 | 1/2002 |

(Continued)

OTHER PUBLICATIONS

Genbank Accession No. AOB54356.1 (Year: 2015).*

(Continued)

*Primary Examiner* — M Franco G Salvoza
(74) *Attorney, Agent, or Firm* — Michael D. Davis

(57) ABSTRACT

The present invention relates to the stabilisation of foot-and-mouth disease virus (FMDV) capsids, by specific substitution of amino acids in a specific region of FMDV VP2. The invention provides stabilised FMDV capsids and vaccines against FMD.

9 Claims, 10 Drawing Sheets

Figure 1:
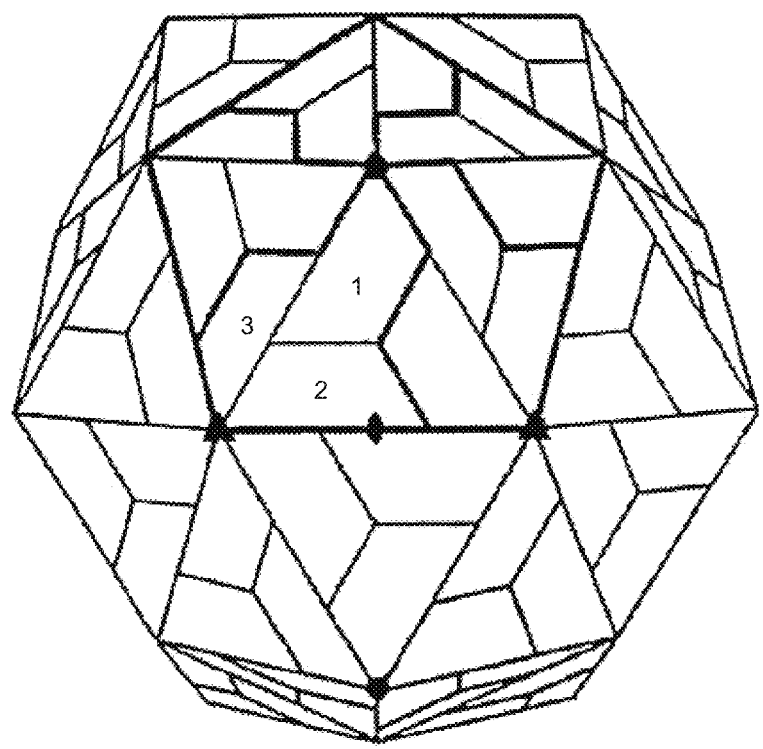

Specification includes a Sequence Listing.

(56) References Cited

FOREIGN PATENT DOCUMENTS

| | | |
|---|---|---|
| WO | 2011007339 A2 | 1/2011 |
| WO | 2011048353 A2 | 4/2011 |
| WO | 2011054011 A2 | 5/2011 |
| WO | 2011112945 A2 | 9/2011 |
| WO | 2012032348 A1 | 3/2012 |

OTHER PUBLICATIONS

Genbank Accession No. AOC15457.1 (Year: 2015).*
Abrams, et al, Assembly of foot-and-mouth disease virus empty capsids synthesized by a vaccinia virus expression system, Journal of General Virology, 1995, 3089-3098, 76.
Acharya, Ravindra et al, The three-dimensional structure of foot-and-mouth disease virus at 2.9 A resolution, Nature, 1989, 709, 337.
Cao, Yi-Mei, et al, Synthesis of foot-and-mouth disease virus empty capsids in insect, 2009.
Curry, S et al, Viral RNA modulates the acid sensitivity of foot-and-mouth disease virus capsids, Journal of Virology, 1995, pp. 430, vol. 69(1).
Doel, et al, Thermal Stability of Foot-and-Mouth Disease Virus, Archives of Virology, 1981, 21-32, 70.
Ellard et al, Evidence for the role of His-142 of protein 1C in the acidinduced disassembly of foot-and-mouth disease virus capsids, Journal of General Virology, 1999, pp. 1911, vol. 80.
European Search report for 13161139.4 dated Sep. 24, 2013.
Fry et al, The Structure of Foot-and-Mouth Disease Virus, CTMI, 2005, p. 71-101, 288.
Harmsen., M et al, Effect of thiomersal on dissociation of intact (146S) foot-and-mouth disease virions into 12S particles as assessed by novel ELISAs specific for either 146S or 12S particles, Vaccine, 2011, 2682-2690, 29, Elsevier.
Hegde, et al, Thermostable foot-and-mouth disease virus as a vaccine candidate for endemic countries: A perspective, Vaccine, 2009, 2199-2201, 27, Elsevier.
International Search report for PCTEP2014055904, dated Jun. 17, 2014, 5 pages.
Kim, Suk-Am et al, DNA vaccination against foot-and-mouth disease via electroporation: study of molecular approaches for enhancing VP1 antigenicity, The journal of gene medicine, 2006, 1182-1191, 8.
Kotecha et al, Structure-based energetics of protein interfaces guides foot-and-mouth disease virus vaccine design, Nature structural & molecular biology, 2015, pp. 788-794, vol. 22 No. 10.
Lea, S et al., Supporting document, Protein—NCBI, 1994, 9 pages, Accession P49303.
Lea, S et al., The structure and antigenicity of a type C foot-and-mouth disease virus, Structure, 1994, pp. 123-139, 2.
Lee et al, Production of FMDV virus-like particles by a SUMO fusion protein approach in *Escherichia coli*, Journal of Biomedical Science, Aug. 2009, pp. 69, vol. 16.
Lewis, et al, Expression, Processing, and Assembly of Foot-and-Mouth Disease Virus Capsid Structures in Heterologous Systems: Induction of a Neutralizing Antibody Response in Guinea Pigs, Journal of Virology, Dec. 1991, p. 6572-6580, vol. 65, No. 12.
Liu, Guangqing et al, Generation of an infectious cDNA cvlone of an FMDV strain isolated from swine, Virus Research, 2004, 157-164, 104, Elsevier.
Lu, et al, Protection of guinea pigs and swine by a recombinant adenovirus expressing O serotype of foot-and-mouth disease virus whole capsid and 3C protease, Vaccine, 2008, G48-G53, vol. 26S, Elsevier.
Machine translation of CN101270155, dated Jul. 17, 2017, 28pages.
Martin, et al, A Single Amino Acid Substitution in the Capsid of Foot-and-Mouth Disease Virus Can Increase Acid Resistance, Journal of Virology, Mar. 2011, 2733, vol. 85, No. 6.
Mateo, et al, Engineering Viable Foot-and-Mouth Disease Viruses with Increased Thermostability as a Step in the Development of Improved Vaccines, Journal of Virology, 2008, 12232-12240, 82(24).
Mateu, et al, Virus engineering: functionalization and stabilization, Protein Engineering, Design & Selection, 2011, 53-63, 24.
Porta, et al, Rational Engineering of Recombinant Piconavirus capsids to Procedure Safe, Protective Vaccine Antigen, PLOS Pathogens, 2013, 1-8, vol. 9.
Robertson, BH, Nucleotide and amino sequence coding for polypeptides of foot-and-mouth disease virus type A12, Journal of Virology, 1985, pp. 651-660, 54(3).
Rweyemamu et al, Stability and Immnnogenicity of Empty Particles of Foot-and-Mouth Disease Virus, Archives of Virology, 1979, pp. 69, vol. 59v.
Subramanian, B. Mohana et al, Development of foot-and-mouth disease virus (FMDV) serotype O virus-like-particles (VLPs) vaccine and evaluation of its potency, Antiviral Research, 2012, 288-295, 96, Elsevier.
Twomey, T et al, Characterization of an Acid-Resistant Mutant of Foot-and-Mouth Disease ViruS, Virology, 1995, 69-75, 206.
Walter, Thomas S., A plate-based high-throughput assay for virus stability and vaccine formulation, Journal of Virological Methods, 2012, 166-170, 185, Elsevier.
Wang, Xiangxi et al, A sensor-adaptor mechanism for enterovirus uncoating from structures of EV7, Nature Structural & Molecular Biology, Apr. 2012, 424-430, vol. 19 . iss 4.
Zibert, A, et al, Infectious Foot-and-Mouth Disease Virus Derived from a Cloned Full-Length Cdna, Journal of Virology, 1990, 2467-2473, 64.
U.S. Appl. No. 14/779,797, filed Sep. 24, 2015.

* cited by examiner

Figure 2

| FMDV Serotypes | 87 | 88 | 89 | 90 | 91 | 92 | 93 | 94 | 95 | 96 | 97 | 98 |
|---|---|---|---|---|---|---|---|---|---|---|---|---|
| O1BFS | H | K | G | V | Y | G | S | L | T | D | S | Y |
| O1M_87 | H | K | G | V | Y | G | S | L | T | D | S | Y |
| CS8c1 | P | K | G | V | Y | G | G | L | V | K | S | Y |
| ASIA1_Bar2003 | H | K | G | V | Y | G | G | L | M | A | S | Y |
| A22_Iraq_95 | H | K | G | V | Y | G | H | L | V | D | S | F |
| SAT1_bot | H | K | G | I | Y | G | Q | L | V | D | S | H |
| SAT2_ZIM7_83 | H | K | G | I | Y | G | S | L | T | D | A | Y |
| SAT3_KNP10_90 | H | K | G | I | Y | G | A | M | L | D | S | H |

Figure 5:

(A)

Wild type      (VP2 S93F)      (VP2 S93H)

(B)

(VP2 S93F)      (VP2 S93Y)      (VP2 S93H)

(B)

(A)

Figure 9

FMDV SAT2 VNT titres

A

B

STABILISED FMDV CAPSIDS

CROSS-REFERENCE TO RELATED APPLICATIONS

This application is a Divisional application of U.S. Ser. No. 14/779,797, filed on Sep. 24, 2015 as a national stage entry under 35 U.S.C. § 371 of PCT/EP2014/055904, filed on Mar. 25, 2014, which claims priority under EP 13161139.4, filed on Mar. 26, 2013, the contents of which are hereby incorporated by reference in their entireties.

The present invention relates to the fields of veterinary medicine and virology. In particular the invention relates to a foot-and-mouth disease virus (FMDV) VP2 protein mutant, an FMDV capsid comprising a FMDV VP2 protein mutant, an isolated nucleic acid molecule, a host cell, a live recombinant carrier micro-organism, and a vaccine against FMD. In addition the invention relates to several methods for, and uses of these embodiments.

Foot-and-mouth disease (FMD) is an acute, systemic, and highly contagious disease affecting cloven-hoofed mammals; the order Artiodactyla. Next to many wild-life species, the main relevant targets are livestock such as cattle, buffalo, swine, sheep, and goats. Typical symptoms are blisters on tongue and hooves; hence the name of the disease. Not only does this cause much discomfort and secondary infections, but also fever and occasional mortality. In addition the disease causes significant economic damage as affected animals will stop moving and feeding. FMD is a notifiable disease and many countries will reject import of animals from FMD positive regions; this is enforced by an international system of export certification (Paton et. al. 2009, Philos. Trans. R. Soc. Lond. B Biol. Sci., vol. 364, p. 2657).

FMD is caused by foot-and-mouth disease virus (FMDV), which is a virus of the Picornaviridae family, and is the type species of the Aphtovirus genus. The virion comprises a single stranded positive sense RNA genome, of about 8 kb, which is contained in a non-enveloped capsid. The capsid is about 30 nm in diameter and has icosahedral symmetry. The capsid consists of a highly regular arrangement of 60 copies of each of four structural viral proteins: VP1, VP2, VP3, and VP4. These are organised in protomer subunits with a sedimentation coefficient of 5S containing one each of VP1-4; five of these protomers form a pentamer of 12S, and the complete capsid consists of 12 pentamers. This can be a non-infectious empty capsid of about 70S, or a virion capsid of about 146S with viral RNA content, which can be infectious (Fry et al., 2005, Curr. Top. Microbiol. Imm., vol. 288, p. 71).

As an icosahedral structure, an FMDV capsid has three natural types of symmetry axis: the 5-fold axis where the protomers meet to assemble into a pentamer, as well as two axes where the pentamer subunits meet: the 2-fold axis of symmetry where neighbouring VP2-VP2 proteins interact, and the 3-fold axis where VP2-VP3 proteins interact; see FIG. 1.

In the native replication the FMDV viral proteins are expressed as a long polyprotein precursor, named P1, which comprises VP4-2-3-1. This is also why the FMDV VP's are sometimes named by their order on P1, whereby: VP1 is 1D, VP2 1B, VP3 10, and VP4 is named 1A. The post-translational cleavage of P1 into smaller parts is done by non-structural FMDV encoded proteins 2 A-C and 3 A-D. (Chapter: Picornaviridae, in: Fields Virology, 4th Edition, Lippincott Williams & Wilkins, ISBN-10: 0781718325)

To reduce the occurrence or the severity of FMD, as well as the spread of FMDV, typical measures are vaccination, selective culling, and movement restrictions. However, some countries allow vaccination only in outbreak conditions, because the system of export certification condemns an animal by whether it is positive for FMDV serology. Marker vaccines that allow the differentiation between vaccination and wild-type infection are therefore being investigated.

Traditional FMD vaccines are adjuvated emulsions of inactivated whole virus preparations, which induce protective levels of virus-neutralising antibodies. However, because of the high infectivity of an FMDV particle, the handling of the virus, and the production of such vaccines needs to be performed under high-level bio-security conditions, and requires effective quality control, especially on virus inactivation.

FMDV is a highly variable agent, and currently has seven main serotypes: O, A, C, SAT (South African territories)-1, SAT-2, and SAT-3, and Asia 1. Within these serogroups there are many antigenic variants, subtypes, and quasi-species. Informative is Carrillo et al. (2005, J. of Gen. Virol., vol. 79, p. 6487) who have aligned the translated genome sequences of over 100 FMDV isolates from all serotypes.

As there is little cross-protection between the main serotypes, typically an FMD vaccine will comprise a separate component for each serotype against which it needs to protect, typically as a combination vaccine.

In respect of prevalence, serotypes A and O have an almost worldwide presence, whereas serotype C has not given any outbreak since 2004. The three SAT serotypes occur in several regions of Africa and the Middle East, and serotype Asia 1 in Asia and the Middle East.

The seven serotypes also differ in biophysical properties, mainly in their stability. This is relevant as FMDV, next to being highly contagious, is also quite unstable, and is readily inactivated by heat, acidity, shear, etc. Nevertheless, all FMD vaccines need to be shipped and stored under strict cold-chain logistics. This is a special handicap in the (sub-) tropical- and developing regions of the world where FMD is endemic. In this respect the virions of serotype A and Asia 1 are relatively more stable than those of other serotypes, and have a workable shelf-life of 6 months or more. However, serotype O vaccines have very limited biological half-life, typically only a few months. Even worse is the situation for the three SAT serotypes, for which the notoriously low stability only yield vaccines of low protective capacity, even when administered multiple times.

Consequently, the development and improvement of safe, stable and effective FMD vaccines is a continued need.

FMD vaccines made by recombinant DNA expression technology have also been investigated for many years. For example by the expression of FMDV subunits or -epitopes in a variety of systems, such as cell-free expression, or cell based expression in prokaryotic or eukaryotic cells, including plant cells.

Another option is the use of empty FMDV capsids; these are safer to produce than whole virus, and were found to be effective immunogens (Rweyemamu, et al., 1979, Arch. Virol., vol. 59, p. 69). Such empty capsids can be produced efficiently in a recombinant expression system, such as based on E. coli (Lewis et al., 1991, J. of Virol., vol. 65, p. 6572; Lee et. al., 2009, J. Biomed. Sci., vol. 16, p. 69), or a viral expression system, e.g. using recombinant Vaccinia virus (Abrams et al., 1995, J. of Gen. Virol., vol. 76, p. 3089); recombinant Baculovirus, either using insect cells (Cao et al., 2009, Vet. Microbiol., vol. 137, p. 1; Charleston et al., WO 2011/048353; Subramanian et al., 2012, Antivir. Res., vol. 96, p. 288), or silkworms (Li et al., 2012, PLoS One. 2012; 7(8): e43849); or a live recombinant vector such as recombinant Adenovirus (Lu et al., 2008, vaccine, vol. 26, Suppl. 6, p. G48).

Unfortunately empty capsids were often found to be even less stable than virion capsids; apparently the viral RNA genome itself provides some stabilising effect to an FMDV capsid structure.

Several groups have investigated the stability characteristics of an FMDV capsid, which rapidly dissociates into pentamers above physiological temperatures and below physiological pH. For vaccine use this is unfavourable, as the 12S pentamers are much less immunogenic than the intact capsids. See: Doel et al. (1981, Arch. of Virol., vol. 70, p. 21), and Hegde et al. (2009, in: Editorial, Vaccine, vol. 27, p. 2199). Twomey et al. (1995, Virology, vol. 206, p. 69) studied natural variants of FMDV A serotype that were less acid-sensitive resulting from amino acid substitutions at positions 131 and 133 of VP2 protein.

To improve the thermo- and/or the acid stability of an FMDV capsid, several groups have introduced mutations into one or more of the viral structural proteins, and then used such VP mutants to produce FMDV virion capsids, and tested these for their bio-physical properties; so-called capsid engineering.

In general successes varied; to some extent acid sensitivity could be decreased by mutations to Histidine residues in positions 140-145 of VP3: Martin-Acebes et al., (2011, J. of Virol., vol. 85, p. 2733), Liu et al. (CN 101270155), and Ellard et al. (1999, J. of Gen. Virol., vol. 80, p. 1911). Martin-Acebes et al. (supra) substituted: VP1 N17D (meaning: the substitution in VP1 of Asparagine at position 17 by Aspartic acid).

In a similar way the FMDV capsid thermo-stability could be somewhat improved by mutation of amino acids in a number of regions of VP2 and of VP3 proteins: Mateo et al. (2008, J. of Virol., vol. 82, p. 12232), King et al. (WO 2002/000251), and Fowler et al. (WO 2011/032348). For a review: Mateu (2011, Prot. Eng., Des. & Sel., vol. 24, p. 53). Mateo et al. (supra) applied the substitution VP2 A65H, and the combined substitution: VP3 D69E/VP2 I188A. Fowler et al. (supra) substituted: in VP2: L785, E79A, K80R, T88A, E131K, or A193S; and in VP3: H85P or E196A.

The approach by King et al. (supra) differed from this work in that they attempted to stabilise an FMDV capsid by introduction of a covalent—rather than a non-covalent bond. By substitution of a VP2 amino acid for a Cysteine, they introduced a non-natural disulphide bridge between the two adjoining VP2 proteins at the 2-fold axis of symmetry. However, this approach is only applicable for stabilising empty capsids, and not for virion capsids. This is because in this method the resulting capsids are permanently fixed and virion capsids can no longer un-coat upon infection of a host cell.

The amino acid substituted by King et al. (supra) was located at position 93 of VP2 protein (which is described in WO 2002/000251 as amino acid number 179 of its sequence identifier no. 38). This amino acid position is in the region of VP2 protein that in its native structure folds into an α-helix: the VP2 protein αA helix, covering (for O serotype) VP2 amino acids 88-98 (see: Acharya et al., 1989, Nature, vol. 337, p. 709). This region was also studied in relation to the mechanism of un-coating of another Picornavirus, the human Enterovirus (Wang et al., 2012, Nature Str. & Mol. Biol., vol. 19, p. 424), however, the mechanism differs from that of FMDV. Wang et al. did not make or suggest any mutations in this area.

In spite of all the efforts in the prior art, no generally applicable and immunologically effective FMD vaccine, based on engineered FMDV capsids, is currently available.

It is an object of the present invention to provide an alternative FMD vaccine that is applicable to all FMDV serotypes, and that can be based either on FMDV empty capsids, or on FMDV virion capsids. It is a further objective to provide an improved FMD vaccine.

When the inventors attempted to apply the technology described by King et al. (supra), they were disappointed to be unable to apply this approach to generate empty FMDV capsids of a serotype other than A type. For example, Cysteine substitutions were made in the αA helix of a VP2 protein from FMDV of serotype O, either at position 93, or at other positions in the helix. The production of empty capsids was attempted, however either no capsids would form at all, or the capsids would be severely aggregated, making them unusable for vaccine purposes.

Surprisingly it was found that this object can be met, and consequently disadvantages of the prior art can be overcome, by providing an FMDV VP2 protein mutant that comprises a specific amino acid substitution in the region of the αA helix of VP2 protein, without requiring the introduction of a covalent bond.

Such an FMDV VP2 protein mutant can now be incorporated into FMDV capsids, which then obtain a significantly improved biophysical stability. The resulting stabilised FMDV capsids can now be used to produce advantageous FMD vaccines based on virion capsids or on empty capsids.

While the exact mechanism of action is not known, and without being bound by any theory or model, the inventors speculate that the advantageous effect of such a substitution in this region is that this provides hydrophobic and/or electrostatic stabilisation at the molecular level to an FMDV capsid. Assumedly this occurs by enhancing the intermolecular interactions between two adjoining VP2 proteins in the region of the 2-fold symmetry axis of an FMDV capsid. This strengthens the interaction between neighbouring pentamers, which results in a significantly improved stability of an FMDV capsid as a whole.

The improved stability of FMDV capsid results in a number of advantages over FMDV capsids with unmodified parental VP2 protein: the VP2 protein mutant-containing capsids can be produced to higher amounts, they can be transported with less strict requirement on cold-chain logistics, and they provide an improved immune-response.

All this was unexpected, as no non-covalent bond mutations have previously been described for this specific region of VP2 protein, or could have been expected to result in such significant improvements to FMDV capsid stability, and to an FMD vaccine produced therefrom.

Therefore in one aspect the invention relates to a foot-and-mouth disease virus (FMDV) VP2 protein mutant, characterised in that the VP2 protein mutant comprises at least one substitution of an amino acid located in the αA helix of the VP2 protein, for an amino acid selected from the group consisting of: Q, N, V, I, L, M, F, Y, W, and H.

A "foot-and-mouth disease virus" for the invention is a virus having the characterising features of a member of the taxonomic species FMDV. This includes also FMDV that are sub-classified therefrom in any way, for instance as a subspecies, quasispecies, strain, isolate, genotype, serotype, serovar, variant or subtype and the like. It will be apparent to a skilled person that while a micro-organism may be currently named FMDV, this is a taxonomic classification which could be subject to change as new insights lead to reclassification into a new or different taxonomic group. However, as this does not change the micro-organism involved or its characterising features, only its name or classification, such re-classified organisms are considered to remain within the scope of the invention.

A "VP2 protein" for the invention refers to the viral protein number 2 of FMDV, which is known as a structural protein of an FMDV capsid. It has about 218 amino acids, and a molecular weight of about 24 kDa. As the skilled person readily appreciates, the variability that is inherent to FMDV means that variations to the size and amino acid sequence of VP2 protein will occur in nature. The amino acid sequence of the VP2 protein from a large number of FMDV isolates is publicly available from sequence databases such as GENBANK™, or SWISS PROT™.

The VP2 protein mutant according to the invention may be of biologic or synthetic origin, and may be obtained by isolation, purification, assembly etc. Preferably the VP2 protein mutant is obtained through the use of recombinant expression technology, by expression of a nucleotide sequence encoding the VP2 protein mutant.

A VP2 protein for use in the invention can be obtained from an FMDV, e.g. by obtaining the VP2 protein encoding nucleic acid from an FMDV, or the nucleotide sequence thereof. Such an FMDV in turn can be obtained (with appropriate bio-security measures) from a variety of sources, e.g. as original field isolate, or from depositary institutions such as ATCC, or CNCM, or from various laboratories and (reference-) institutions, such as the Pirbright Institute (Pirbright, Woking, UK), which is the FAO and WHO world reference laboratory for FMD (WRL FMD).

FMDV for use in the invention are one or more FMDV of the A, O, C, SAT-1, SAT-2, SAT-3, or Asia1 serotype(s); preferably FMDV for use in the invention are one or more FMDV that are circulating in the field at a certain time.

More preferred are one or more FMDV from O, SAT-1, SAT-2, or SAT-3 serotypes, as for these serotypes lack of stability issues have the most impact in the field.

Alternatively, preferred FMDV are those that are recommended by the WRL FMD as high priority vaccine candidates; e.g. in their latest report these are: O Manisa, O PanAsia-2, O BFS, O Campos, A 24 Cruzeiro, Asia 1 Shamir, A Iran-05, A 22 Iraq, SAT-2 Saudi Arabia, and SAT-2 Eritrea, or an equivalent of any of these (WRL FMD Quarterly report, October-December 2012).

A "mutant" for the invention, is an entity that was not previously publicly known or available, either from nature or from the laboratory. The FMDV VP2 protein mutant according to the invention thus differs from a VP2 protein that was described in the prior art before the present invention. In particular, no FMDV VP2 protein amino acid sequence known to date qualifies as a VP2 protein mutant according to the invention. Nevertheless, a VP2 protein mutant according to the invention may be obtained from nature, but preferably is man-made.

Therefore, in one embodiment the FMDV VP2 protein mutant according to the invention comprises at least one substitution of an amino acid located in the αA helix of the VP2 protein, for an amino acid selected from the group consisting of: Q, N, V, I, L, M, F, Y, W, and H, with the proviso that the substitution does not result in a VP2 protein with an amino acid sequence known in the prior art.

Therefore in a further embodiment the FMDV VP2 protein mutant according to the invention comprises at least one substitution of an amino acid located in the αA helix of the VP2 protein, for an amino acid selected from the group consisting of: Q, N, V, I, L, M, F, Y, W, and H, with the proviso that the substitution does not result in a VP2 protein with one or more (or all) of the following amino acid sequence(s):

90V in FMDV of serotype 0 (e.g. as in strain O1BFS and/or O1M_87), and/or not 90V in serotype C (e.g. CS8c1), and/or not 90V in serotype Asia 1 (e.g. ASIA1_Bar2003), and/or not 90V in serotype A (e.g. A22_Iraq_95), and/or not 90I in serotype SAT-1 (e.g. SAT1_bot), and/or not 90I in serotype SAT-2 (e.g. SAT2_ZIM7_83), and/or not 90I in serotype SAT-3 (e.g. SAT3_KNP10_90).

91Y.

93H in FMDV of serotype A (e.g. as in strain A22_Iraq_95), and/or not 93Q in serotype SAT-1 (e.g. SAT1_bot).

94L in FMDV of serotype O (e.g. as in strain O1 BFS and/or O1M_87), and/or not 94L in serotype C (e.g. CS8c1), and/or not 94L in serotype Asia 1 (e.g. ASIA1_Bar2003), and/or not 94L in serotype A (e.g. A22_Iraq_95), and/or not 94L in serotype SAT-1 (e.g. SAT1_bot), and/or not 94L in serotype SAT-2 (e.g. SAT2_ZIM7_83), and/or not 94M in serotype SAT-3 (e.g. SAT3_KNP10_90).

95V in FMDV of serotype C (e.g. as in strain CS8c1), and/or not 95M in serotype Asia 1 (e.g. as in strain ASIA1_Bar2003), and/or not 95V in serotype A (e.g. A22_Iraq_95), and/or not 95V in serotype SAT-1 (e.g. SAT1_bot), and/or not 95L in serotype SAT-3 (e.g. SAT3_KNP10_90).

98Y in FMDV of serotype O (e.g. as in strain O1BFS and/or O1M_87), and/or not 98Y in serotype C (e.g. CS8c1), and/or not 98Y in serotype Asia 1 (e.g. ASIA1_Bar2003), and/or not 98F in serotype A (e.g. A22_Iraq_95), and/or not 98H in serotype SAT-1 (e.g. SAT1_bot), and/or not 98Y in serotype SAT-2 (e.g. SAT2_ZIM7_83), and/or not 98H in serotype SAT-3 (e.g. SAT3_KNP10_90).

Methods to obtain such a VP2 protein mutant according to the invention can be based on a random or a directed approach; for example mutants can be identified and selected from random field-isolates. Also, virus-cell passages can be performed to induce mutations, e.g. by passaging FMDV in the presence of a mutagenic substance, followed by selection for an FMDV comprising a VP2 protein mutant according to the invention, resulting in a more stable capsid. Such stability can be tested by applying a selective level of acidity, temperature, shear, chemicals, etc., comparing the passaged—to the unpassaged isolates in respect of intactness, and infectivity, for example as described and exemplified herein.

In a preferred embodiment a VP2 protein mutant according to the invention was ranked using in silico methods for structural analysis, and prepared using directed molecular biological techniques, involving e.g. cloning, transfection, recombination, selection, and amplification. Such techniques are extensively described in well-known handbooks such as: Current Protocols in Molecular Biology, John Wiley & Sons, N.Y. (1989); Basic Methods in Molecular Biology, Elsevier Science Publishing Co., Inc., N.Y. (1986); and: Sambrook & Russell, 2001, in: 'Molecular cloning: a laboratory manual', 3rd edn. New York, USA: Cold Spring Harbour Laboratory Press.

Detailed methods for mutation of VP2 protein are also described and exemplified herein. Therefore, a person skilled in the art will readily be able to apply, adapt, modify and improve upon these techniques, using nothing but routine methods and materials.

The term "comprises" (as well as variations such as "comprise", "comprised", and "comprising") as used herein, intends to refer to all elements, and in any possible combination conceivable for the invention, that are covered by or included in the text section, paragraph, claim, etc., in which this term is used, even if such elements or combinations are not explicitly recited; and not to the exclusion of any of such element(s) or combinations. Therefore any such text section, paragraph, claim, etc., can also relate to one or more embodiment(s) wherein the term "comprises" (or its variants) is replaced by terms such as "consist of", "consisting of", or "consist essentially of".

A "substitution" is a replacement of one element for another; for the invention this is a mutation which regards the replacement of one amino acid or nucleic acid by another, depending on whether the subject is a protein, a DNA or an RNA molecule. The element that is replaced is the element that occurs in the unmodified parental, or wildtype version of the protein or nucleic acid. As a result, a substitution according to the invention leads to an αA helix that differs from its parental, or wildtype αA helix, i.e. it leads to a modified αA helix that differs from the αA helix wild type version. Any wild type αA helix has the stability issue addressed here above. The current invention leads to an αA helix that is not known from nature and improved with respect to its property to stabilize empty capsids.

The "αA helix" is a region of an FMDV VP2 protein that can fold into an alpha helix structure in the native capsid conformation.

To serve as a reference for the invention, "SEQ ID NO: 1" presents the amino acid sequence of the VP2 protein, taken from the P1 protein of FMDV serotype O, strain 1 BFS, published under GenBank accession number: AAT01758; the VP2 protein is the section of amino acids no. 287-504 of the complete P1 polyprotein. In SEQ ID NO: 1 the αA helix is 12 amino acids long, and is located from amino acid position 87 up to and including position 98.

The inherent variability of FMDV means that the position of this αA helix in VP2 protein of other FMDV isolates or serotypes is not in the exact same position, e.g. it can be offset by one or more amino acids, in either the N-terminal or C-terminal direction. Nevertheless the αA helix can easily be identified in the VP2 amino acid sequence, using for example a standard computer program for molecular-biological analysis. Consequently, for the invention the amino acid position numbers of the VP2 αA helix are specified relative to SEQ ID NO: 1, but in different FMDV isolates these may be located at different position numbers.

Therefore, for the invention the αA helix of a VP2 protein is a region of about 12 amino acids long, that is located in a region corresponding to the range between VP2 amino acid position numbers 87 and 98, whereby these position numbers are relative to the numbering of the amino acids presented in SEQ ID NO: 1.

Preferably the αA helix of a VP2 protein is located from amino acid position number 87 up to and including position 98, whereby these position numbers are relative to the numbering of the amino acids presented in SEQ ID NO: 1.

Merely to illustrate the level of sequence variability that occurs between different FMDV isolates known at the filing date, FIG. 2 presents a multiple alignment of the amino acid sequence of the αA helix of VP2 protein for a number of representative FMDV isolates. Carrillo et al. (supra) indicates that the only generally conserved amino acids in the VP2 protein αA helix region are the Glycines at positions 89 and 92 (relative to the numbering of the amino acids presented in SEQ ID NO: 1).

The amino acids: "Q, N, V, I, L, M, F, Y, W, and H" are represented in the well-known 1-letter code according to the IUPAC standard. In 3-letter IUPAC standard code this summation would read: "Gln, Asn, Val, Ile, Leu, Met, Phe, Tyr, Trp, and His". Of these amino acids, Q and N have a polar, uncharged side chain, as usually does also H; V, I, L, M, F, Y, and W have a hydrophobic side chain; and amino acids F, Y, W, and H have an aromatic side chain.

Preferred amino acids to be substituted for, are one or more amino acids with a hydrophobic side chain selected from the group consisting of: V, I, L, M, F, Y, and W, or one or more amino acids with an aromatic side chain selected from the group consisting of: F, Y, W, and H. More preferred amino acids to be substituted for, are one or more amino acids with an aromatic side chain selected from the group consisting of: F, Y, W, and H.

This preference is based on the surprising finding that amino acids with hydrophobic side chains, and especially amino acids with aromatic side chains, even though being relatively large, fitted unexpectedly well into the area of an FMDV capsid at the 2-fold symmetry axis, and were found to provide a significant stabilising effect to an FMDV capsid comprising a VP2 protein mutant with such a substitution.

For the invention, an aromatic amino acid is an amino acid having an aromatic side chain. A side chain is aromatic when it comprises a ring structure that complies with Hackers rule.

In some positions of the VP2 protein αA helix, amino acid substitutions according to the invention were especially advantageous.

Therefore, in a preferred embodiment of an FMDV VP2 protein mutant according to the invention, the invention regards the substitution of an amino acid in at least one position selected from the group consisting of: 87, 90, 91, 93, 94, 97, and 98, wherein the VP2 protein amino acid position numbers are relative to the numbering of the amino acids presented in SEQ ID NO: 1.

In a preferred embodiment a position in the VP2 protein αA helix for substitution for the invention is one or more position in the VP2 protein αA helix at 87 and/or at 98, wherein the VP2 protein amino acid position numbers are relative to the numbering of the amino acids presented in SEQ ID NO: 1. At these amino acid positions, located at the N- and C-termini of the VP2 protein αA helix, substitutions were surprisingly found to be able to stabilise an FMDV capsid containing such a VP2 protein mutant.

In a preferred embodiment the positions in the VP2 protein αA helix for substitution for the invention are one or more of: 90, 93, and 97, wherein the VP2 protein amino acid position number is relative to the numbering of the amino acids presented in SEQ ID NO: 1. The inventors have found that the side chain of amino acids in these positions in the VP2 protein αA helix is orientated towards the opposing VP2 protein across the 2-fold symmetry axis. This allowed selected mutations in these positions to have a stabilising effect on the capsid.

Consequently, non-covalent molecular interactions that are induced by the amino acid substitutions in these positions, work effectively in stabilisation across the 2-fold symmetry axis.

In a more preferred embodiment the position in the VP2 protein αA helix for substitution for the invention is position number 93, relative to the numbering of the amino acids presented in SEQ ID NO: 1. This amino acid position was found to be located in the middle of the VP2 protein αA helix, with its amino acid side chain directed towards the equivalent residue in the opposing VP2 protein. Consequently, when a substitution is made to the amino acid sequence of an FMDV VP2 protein in this position, this can form a non-covalent interaction across the 2-fold symmetry axis which can considerably stabilise an FMDV capsid containing such a VP2 protein mutant.

Figure 3:
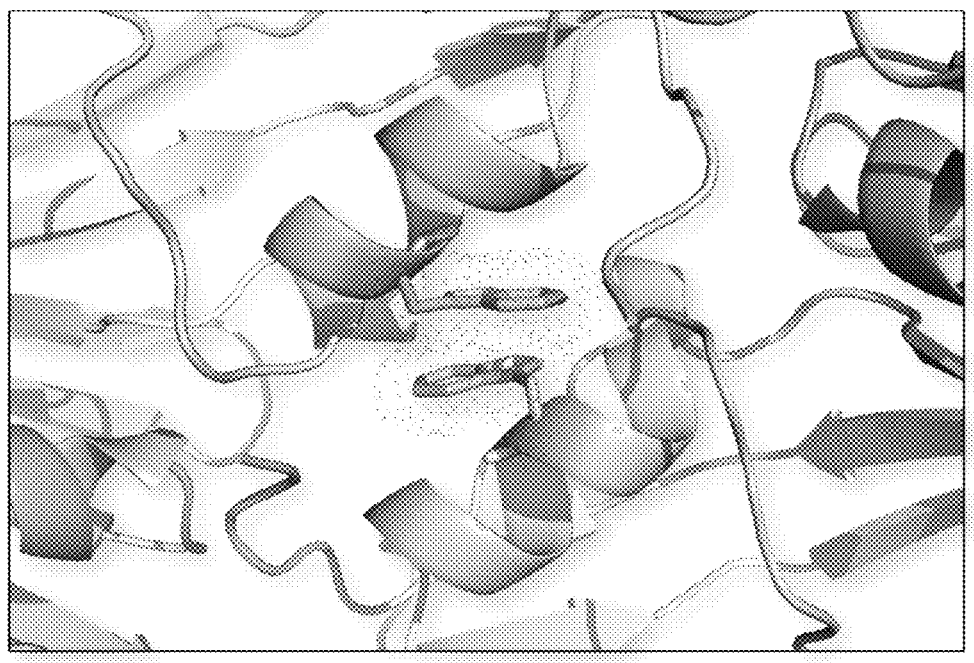

As an illustration, FIG. 3 presents a 3D image of a non-covalent (hydrophobic stacking) interaction formed across the two-fold symmetry axis in an FMDV capsid comprising a VP2 93W substitution.

For the invention, a non-covalent chemical interaction is an inter-molecular interaction by way of atomic forces such as ionic-, hydrogen-, van der Waals or hydrophobic interactions.

In a further preferred embodiment of an FMDV VP2 protein mutant according to the invention, the VP2 protein mutant comprises at least one substitution for an amino acid selected from the group consisting of: 87V, 87M; 90N, 90L; 91F; 93Y, 93F, 93W, 93H, 93V, 93L, 93I, 93M, 93Q; 94V; 97I, 97M, 97V, 97Q; 98F and 98H, wherein the VP2 protein amino acid position number is relative to the numbering of the amino acids presented in SEQ ID NO: 1.

As described above, this embodiment is also under the proviso that the substitution of an amino acid in VP2 does not result in one or more (or all) of the following amino acid sequences known in the prior art on FMDV VP2 proteins:
  93H in FMDV of serotype A, and/or not 93Q in serotype SAT-1,
  98F in serotype A, and/or not 98H in serotype SAT-1, and/or not 98H in serotype SAT-3.

For the invention, a notation such as "VP2 93F", is intended to indicate the substitution of any parental amino acid in VP2 at amino acid position number 93 (relative to the numbering of the amino acids presented in SEQ ID NO: 1) for the indicated amino acid (here: phenylalanine).

Combinations of more than one of the preferred amino acid substitutions are also within the scope of the present invention. Thus, for example, the VP2 protein mutant of the present invention may comprise a 93Y, 93F or 93H substitution along with a 97I or 97M and/or a 90N substitution. Other examples of specific combinations of substitutions that are within the scope of the present invention include VP2 protein mutants with double substitutions selected from the group consisting of: 93Y and 97I; 90N and 93Y; 87V and 93F; 93H and 98F; 93F and 98F; 91F and 98F; 95V and 98F; and 87V and 98F. In one embodiment, the present invention includes VP2 protein mutants, with triple substitutions selected from the group consisting of: 93H, 95V and 98F; 93F, 94V and 98F; 87V, 90L and 93Q; 90L, 93Q, and 98F; and 90A, 93Q and 98F. An example of a VP2 protein mutant with 4 substitutions is a VP2 protein mutant with: 87V, 90L, 93Y and 97I. All VP2 protein amino acid position numbers are relative to the numbering of the amino acids presented in SEQ ID NO: 1.

In one embodiment the FMDV VP2 protein mutant according to the invention comprises at least one substitution for an amino acid selected from the group consisting of: 93Y, 93F, 93W, 93H, 93V, 93L, 93I, 93M, and 93Q, wherein the VP2 protein amino acid position number is relative to the numbering of the amino acids presented in SEQ ID NO: 1, with the proviso that the substitution does not result in a VP2 protein with one or more (or all) of the following amino acid sequence(s): 93H in FMDV of serotype A, and/or not 93Q in serotype SAT-1.

In one embodiment, an FMDV VP2 protein mutant according to the invention comprises at least one amino acid substitution for an amino acid selected from the group consisting of: 93Y, 93F, 93W, 93V, 93L, 93I and 93M, wherein the VP2 protein amino acid position number is relative to the numbering of the amino acids presented in SEQ ID NO: 1.

In one embodiment the FMDV VP2 protein mutant according to the invention comprises at least one substitution for an amino acid selected from the group consisting of: 93Y, 93F, 93W, and 93H, wherein the VP2 protein amino acid position number is relative to the numbering of the amino acids presented in SEQ ID NO: 1, with the proviso that the substitution does not result in a VP2 protein with the amino acid sequence 93H in FMDV of serotype A.

In one embodiment the FMDV VP2 protein mutant according to the invention comprises at least one substitution for an amino acid selected from the group consisting of: 98F and 98H, wherein the VP2 protein amino acid position number is relative to the numbering of the amino acids presented in SEQ ID NO: 1, with the proviso that the substitution does not result in a VP2 protein with one or more (or all) of the following amino acid sequence(s): 98F in FMDV of serotype A, and/or not 98H in serotype SAT-1, and/or not 98H in serotype SAT-3.

In one embodiment the FMDV VP2 protein mutant according to the invention is a VP2 protein from an FMDV of a serotype selected from the group consisting of serotypes: O, Asia 1, SAT-1, SAT-2, and SAT-3, which VP2 comprises an amino acid substitution for an amino acid selected from the group consisting of: 93Y, 93F, 93W, and 93H, wherein the VP2 protein amino acid position number is relative to the numbering of the amino acids presented in SEQ ID NO: 1.

In one embodiment the FMDV VP2 protein mutant according to the invention is a VP2 protein from an FMDV of a serotype selected from the group consisting of serotypes: A, O, Asia 1, SAT-2, and SAT-3, which VP2 comprises an amino acid substitution for an amino acid selected from the group consisting of: 93Y, 93F, 93W, 93H, and 93Q, wherein the VP2 protein amino acid position number is relative to the numbering of the amino acids presented in SEQ ID NO: 1.

In a preferred embodiment the FMDV VP2 protein mutant according to the invention is a VP2 protein from an FMDV of any serotype, which VP2 protein mutant comprises an amino acid substitution for an amino acid selected from the group consisting of: 93Y, 93F, and 93W, wherein the VP2 protein amino acid position number is relative to the numbering of the amino acids presented in SEQ ID NO: 1. As is described below, these substitutions in this position provided FMDV capsids comprising such a VP2 protein mutant with the highest relative stability.

The advantageous amino acid substitutions of a VP2 protein mutant according to the invention have been identified by a combination of methods using in silico, in vitro, and in vivo experiments.

Table 1, in panels A, B, and C, lists the results of the assessment of the stability of FMDV capsids comprising VP2 protein mutants, for different FMDV serotypes. The relative stability of the different VP2 mutant-comprising capsids is indicated by an arbitrary value: '0', or '+', whereby the zero stands for the level of stability of a capsid having unsubstituted parental VP2 protein, the minus sign indicates relatively unstable capsids, i.e. less stable than the parental capsids, and the positive sign indicates relatively stable capsids, i.e. more stable than the parental capsids. Relative differences between mutant capsids are indicated by the number of positive or negative signs, e.g. '++++' is much more stable than '+'.

For illustration, Table 1A also presents the relative stability of some substitutions to VP2 protein that are not considered to stabilise an FMDV capsid, for example: whereas the substitution VP2 H87V in an FMDV of O serotype is beneficial to the capsid's stability (relative score of +), however the substitution H87D is very unfavourable (relative score of ---). Similarly, the resulting relative stability of substitutions to a region of VP2 protein that is outside of the αA helix are presented: VP2 Q57E, Q57L, R60G, and R60L. As these have relative stabilities between -- and ---, consequently these substitutions are detrimental to the stability of an FMDV capsid comprising a VP2 protein mutant with such a substitution.

TABLE 1A

Relative stability of capsids of FMDV from O serotype:

| Mutation | relative stability |
| --- | --- |
| Serotype O | |
| VP2 wt | 0 |
| VP2 H87V | + |
| VP2 H87D | --- |
| VP2 V90N | + |
| VP2 Y91F | ++ |
| VP2 S93H | ++ |
| VP2 S93Y | +++ |
| VP2 S93F | +++ |
| VP2 S93W | ++ |
| VP2 S93Q | ++ |
| VP2 L94V | ++ |
| VP2 S97V | ++ |
| VP2 S97I | ++ |
| VP2 S97Q | ++ |
| VP2 Y98F | +++ |
| VP2 R60G | --- |
| VP2 R60L | --- |
| VP2 Q57E | -- |
| VP2 Q57L | -- |

TABLE 1B

Relative stability of capsids of FMDV from A serotype:

| Mutation | relative stability |
| --- | --- |
| Serotype A | |
| VP2 wt | 0 |
| VP2 H93F | ++ |
| VP2 H93Q | + |

TABLE 1C

Relative stability of capsids of FMDV from SAT-2 serotype:

| Mutation | relative stability |
| --- | --- |
| Serotype SAT-2 | |
| VP2 wt | 0 |
| VP2 S93H | ++ |
| VP2 S93Y | +++ |
| VP2 S93W | ++++ |

TABLE 1C-continued

Relative stability of capsids of FMDV from SAT-2 serotype:

| Mutation | relative stability |
| --- | --- |
| VP2 S93F | +++ |
| VP2 Y98F | ++ |

To generate FMDV VP2 protein mutant-comprising capsids, in vitro recombinant DNA methods were used to generate a recombinant nucleic acid molecule that encoded a VP2 protein mutant according to the invention, comprising the desired amino acid substitution(s). Conveniently this was done by making and sub-cloning PCR fragments, and in vitro protein expression in the context of other FMDV proteins, e.g. as a P1-2A polyprotein, and with co-expression of an FMDV 3C protease.

The required molecular-biological techniques are all well-known to a skilled person, e.g. as described in well-known handbooks such as: 'Current Protocols in Molecular Biology', and 'Molecular cloning: a laboratory manual', both supra.

To generate infectious FMDV virion capsids comprising a VP2 protein mutant according to the invention several techniques are available, for instance using an infectious clone construct of FMDV which can be manipulated as cDNA to encode the desired VP2 protein substitution, and then transfected into appropriate host cells. Infectious clones of FMDV have been known for a long time, e.g. Zibert et al. (1990, J. of Virol., vol. 64, p. 2467); Liu et al. (2004, Virus Res., vol. 104, p. 157); and: Blignaut et al. (2010, J. of Gen. Virol., vol. 92, p. 849).

Alternatively, an FMDV empty capsid can be produced by the expression of an appropriate nucleic acid in a recombinant expression system, such as are described below.

By these technologies, FMDV capsids can be formed, either as empty- or as virion capsids, and comprising a VP2 protein mutant according to the invention.

FMDV virion capsids comprising a VP2 protein mutant according to the invention were isolated from a cell-culture, purified and tested for stability, e.g. in response to elevated temperature, reduced pH, and chemical inactivation. Subsequently the treated virion capsids were tested for intactness, by sucrose gradient, followed by electron microscopy or by gel-electrophoresis, by 12S Elisa (Harmsen et al., 2011, Vaccine, vol. 29, p. 2682), or by thermofluor assay (Walter et al., 2012, J. of Virol. Meth., vol. 185, p. 166). Virion capsids were also tested for viability in plaque assays. The results indicated that the VP2 protein mutations according to the invention enhanced capsid stability significantly.

For example infectious FMDV virion capsids comprising a VP2 protein mutant according to the invention FMDV were obtained of SAT-2 serotype, comprising either the substitution VP2 S93H, or VP2 S93Y. These mutant viruses were tested in a thermofluor assay, and found to be very stable: the S93H mutant was stable up to 51° C., and the S93Y mutant up to 53° C. This is impressive in comparison to the stability of the infectious SAT-2 parental virus, which was only stable up to 47° C. The infectious FMDV virion capsids comprising these VP2 protein mutants did also replicate well on BHK-21 cells, totally comparable to the wildtype virus.

Results are described in the Examples section hereinafter. Methods and materials for performing such procedures are well known in the art, and are described in detail herein. Therefore these can be readily applied by a skilled person, using nothing but routine methods and materials.

Therefore in a further aspect, the invention relates to an FMDV capsid comprising an FMDV VP2 protein mutant according to the invention.

An FMDV "capsid" for the invention is known in the art, and is a macro-molecular structure of icosahedral symmetry, which consists of a highly regular arrangement of FMDV structural viral proteins. An FMDV capsid according to the invention can be an FMDV empty capsid, or an FMDV RNA-containing virion capsid. Such an FMDV virion capsid can be infectious or not, depending on the condition of the viral genetic material it comprises.

In a preferred embodiment, an FMDV capsid according to the invention is an FMDV virion capsid.

An FMDV virion capsid according to the invention can be of any serotype, and can comprise any VP2 protein mutant according to the invention.

In a further preferred embodiment an FMDV virion capsid according to the invention comprises an FMDV VP2 protein mutant according to the invention which VP2 protein mutant comprises an amino acid substitution for an amino acid selected from the group consisting of: 93Y, 93F, 93W and 93H, wherein the VP2 protein amino acid position number is relative to the numbering of the amino acids presented in SEQ ID NO: 1, with the proviso that the substitution does not result in a VP2 protein with the amino acid sequence 93H in FMDV of serotype A.

In a preferred embodiment, an FMDV capsid according to the invention is an FMDV empty capsid.

An FMDV empty capsid according to the invention can be of any serotype, and can comprise any VP2 protein mutant according to the invention.

In a further preferred embodiment an FMDV empty capsid according to the invention comprises an FMDV VP2 protein mutant according to the invention which VP2 protein mutant comprises an amino acid substitution for an amino acid selected from the group consisting of: 93Y, 93F, 93W and 93H, wherein the VP2 protein amino acid position number is relative to the numbering of the amino acids presented in SEQ ID NO: 1, with the proviso that the substitution does not result in a VP2 protein with the amino acid sequence 93H in FMDV of serotype A.

An FMDV capsid according to the invention can be obtained in a variety of ways. For example an FMDV virion capsid according to the invention can be generated by manipulation of FMDV genetic material, transfection into appropriate host cells, and amplification of the resulting infectious FMDV virus comprising an FMDV VP2 protein mutant according to the invention in an appropriate host cell, e.g. BHK-21 cells.

Alternatively, an FMDV empty capsid according to the invention can be produced via an in vitro cell-based expression system, as this provides advantages in respect of yields and safety. The expression system can be based on prokaryotic or eukaryotic cells; when eucaryotic, can be based on host cells from a yeast, mammalian, insect, or plant, all as described in the prior art.

A preferred in vitro expression system for an FMDV empty capsid according to the invention is the Baculovirus/insect cell expression system (BVES), as in this system the advantageous properties of a capsid according to the invention come to their full use. This is because the culture medium normally used for the insect cells of the BVES is rather acidic, typically at a pH of about 6.5. Also a typical expression run on insect cells takes up to 5 days at 27° C. Both conditions are inherently unfavourable for an unstabilised FMDV empty capsid.

Indeed, the expression of wildtype FMDV empty capsids of O serotype or of one of the SAT serotypes in BVES was found not to be very effective and yielded little capsid antigen. However, when they expressed FMDV empty capsids comprising an FMDV VP2 protein mutant according to the invention in the BVES, significant yields of empty capsid antigen could be obtained. Consequently, the stabilised FMDV capsids according to the invention were found to be able to better withstand the conditions of the BVES.

The expression and assembly of empty FMDV capsids according to the invention can be set up in a variety of ways, provided that the FMDV structural proteins, VPs 1, 3, 4 and the VP2 protein mutant, are combined in a way that enables them to assemble into complete empty capsids. In practice this can be set up by simultaneous- or separate expression of the VPs, and by expression in the same or in different host cells. In a preferred embodiment of an expression system for use in the invention, the expression of an FMDV empty capsid according to the invention is by way of co-expression of all FMDV VPs, in the same host cell. This provides the optimal control over the resulting capsid product.

When an FMDV capsid according to the invention is produced in any of these ways, so by replication of a virion capsid, or by expression of an empty capsid, then the VP2 protein in those capsids will in principle consist entirely of VP2 protein mutant according to the invention. This provides the most stable constitution for such a capsid.

Therefore in a preferred embodiment of an FMDV capsid according to the invention, the VP2 protein in the capsid consists essentially of VP2 protein mutant according to the invention.

Nevertheless, the present invention also allows the generation of FMDV capsids wherein not all the VP2 protein in the capsid is the VP2 protein mutant according to the invention. Either by mixing-in or by co-expression, some molecules of wildtype VP2 protein can be incorporated also, leading to the formation of VP2-chimeric capsids. This can be advantageous in particular when working with infectious FMDV virion capsids according to the invention, as this is a convenient way to fine-tune the stability of the resulting FMDV virion capsid according to the invention. It is conceivable that comprising only VP2 protein mutant in virion capsids could make such capsids too stable for an FMDV to replicate. Consequently, providing for the incorporation of some wildtype VP2 protein into the FMDV virion capsid can reduce the stability to an acceptable level. However, it is preferred to contain as much of the VP2 protein mutant according to the invention as is possible, in order to retain the highest stability allowable for that infectious FMDV.

Therefore in a preferred embodiment of an FMDV capsid according to the invention, the VP2 protein in an FMDV virion capsid consists for more than 50% of VP2 protein mutant according to the invention. More preferably, for more than 60, 70, 80, 90, 95, or 99%, in that order of preference.

The use of the techniques described results in the generation of an FMDV capsid that comprises (some or more) VP2 protein mutant according to the invention. This provides to the capsid advantageous properties and favourable utilities deriving from its enhanced biophysical stability.

Therefore, in a further aspect, the invention relates to a method for enhancing the stability of an FMDV capsid, comprising the step of providing an FMDV capsid with an FMDV VP2 protein mutant according to the invention.

"Enhancing the stability" refers to the improved biophysical stability of VP2 protein mutant-containing FMDV capsids, as compared to wildtype VP2 protein containing capsids. The stability can be improved in respect of different physical parameters, such as temperature, acidity, shear, and other challenges to which an FMDV capsid can be exposed in the course of its generation and its use as a vaccine antigen.

Examples of such challenges in normal vaccine technology are e.g. the chemical inactivation in case of virion capsids, the storage and transport at varying temperatures, as well as the formulation with an adjuvant.

The level of the stability improvement obtained can be assessed using a variety of methods, e.g. sucrose gradient, gel electrophoresis, electron microscopy, thermofluor assay, etc., as is described herein.

Details and embodiments for the step of "providing an FMDV capsid with an FMDV VP2 protein mutant" have been described above, and can conveniently be performed using a variety of recombinant DNA techniques, such as co-expression, and inter-mixing, while the FMDV capsid is forming.

For this and other utilities of generating and applying an FMDV VP2 protein mutant according to the invention, the preferred method is by recombinant DNA technology, which involves the use of a nucleic acid molecule that can express such a VP2 protein mutant according to the invention.

Therefore, in a further aspect, the invention relates to an isolated nucleic acid molecule encoding an FMDV VP2 protein mutant according to the invention.

The term "isolated" is to be interpreted as: isolated from its natural context, by deliberate action or human intervention; e.g. by an in vitro procedure for biochemical purification.

Typically a nucleic acid molecule "encoding" a protein, here: an FMDV VP2 protein mutant according to the invention, is an open reading frame (ORF), indicating that no undesired stop-codons are present that would prematurely terminate the translation into protein. For the invention the nucleic acid molecule encodes the complete FMDV VP2 protein, and it may be of natural or synthetic origin.

For the present invention, the exact nucleotide sequence of a nucleic acid molecule according to the invention is not critical, provided the nucleotide sequence allows the expression of the desired amino acid sequence, here: the desired FMDV VP2 protein mutant. However, as is well known in the art, different nucleic acids can encode the same protein due to the 'degeneracy of the genetic code'. Consequently, two different nucleic acids can have a nucleotide sequence heterogeneity up to 30%, while still encoding the same protein.

For the present invention, a nucleic acid molecule can be a DNA or an RNA molecule. This depends on the source material used for its isolation, and on the intended use. The skilled person is well aware of methods to isolate one or the other type of molecule from a variety of starting materials, and of methods to convert one type into the other.

An isolated nucleic acid molecule according to the invention can conveniently be manipulated in the context of a vector, such as a DNA plasmid, when it is in DNA form. This enables its amplification e.g. in bacterial cultures, and its manipulation by a variety of molecular biological techniques. A wide variety of suitable plasmid vectors is available commercially.

To allow an isolated nucleic acid molecule according to the invention to actually express an FMDV VP2 protein mutant according to the invention, it will require proper expression control signals and a suitable environment. For example a nucleic acid molecule needs to be operatively linked to an upstream promoter element, and needs to contain a translation stop at the end of the coding sequence. Typically the plasmids and vectors used in the context of a particular expression system will provide for such signals. Also, the bio-molecular machinery for transcription and translation is typically provided by a host cell used for such expression. By modifying these various elements, the expression of the VP2 protein mutant according to the invention can be optimised in e.g. timing, level, and quality; all this is within the routine capabilities of the skilled artisan.

Therefore in a preferred embodiment, the isolated nucleic acid molecule according to the invention in addition comprises expression control signals.

A recombinant expression system for use in the invention typically employs a host cell, which can be cultured in vitro. Well known in the art are host cells from bacterial, yeast, fungal, plant, insect, or vertebrate cell expression systems.

Therefore, in a further aspect, the invention relates to a host cell comprising an FMDV VP2 protein mutant according to the invention, an FMDV capsid according to the invention, and/or an isolated nucleic acid molecule according to the invention.

By expression of an isolated nucleic acid molecule according to the invention, a host cell according to the invention can conveniently be used to produce an FMDV VP2 protein mutant according to the invention. Preferably a host cell according to the invention also expresses the other FMDV VPs, and allows the assembly of an FMDV empty capsid according to the invention. Depending on the characteristics and the set-up of the expression system, the empty capsid can then be obtained either from a host cell, e.g. by lysis, or from its culture medium, using downstream processing and purification. Alternatively, a host cell comprising an FMDV VP2 protein mutant or an FMDV empty capsid, both according to the invention, can be used as such, e.g. for use as a vaccine.

A well-known and efficient way to express and/or deliver an FMDV VP2 protein mutant, an FMDV capsid, and/or an isolated nucleic acid molecule, all according to the invention, to a target animal, is by way of a live recombinant carrier micro-organism (LRCM). An LRCM can infect the target animal and replicate in the animal, or in its cells. By this way a nucleic acid molecule, an FMDV VP2 protein mutant, or an FMDV capsid, all according to the invention, are presented to the target animal's immune system in a different way than occurs upon injection as a formulated vaccine. This can provide a more effective immune-stimulation.

Therefore, in a further aspect, the invention relates to a live recombinant carrier micro-organism (LRCM) comprising an isolated nucleic acid molecule according to the invention.

Such LRCMs are e.g. recombinant bacteria, parasites, viruses or yeast cells, able to survive in the animal target that is to be vaccinated against FMD. The delivery of a nucleic acid molecule according to the invention can e.g. stimulate antigen-presenting cells of the target to express it and present the resulting protein to its immune system in the context of MHC1, and/or MHC2, inducing an effective immune response.

A further advantage of LRCM's is their self-propagation, so that only low amounts of the recombinant carrier are necessary for an immunisation.

Therefore preferred LRCMs for the invention are micro-organisms that can replicate in a target animal that needs to be vaccinated against FMD, preferably cattle, buffalo, swine, sheep, and goats. In addition an LRCM should not be (too) pathogenic to the target animal. Examples of such appropriate LRCMs are attenuated or non-pathogenic isolates of bacteria: *E. coli*, Salmonella; parasites: Toxoplasma, or Neospora; or viruses: Pox virus (Vaccinia, cowpox), Adenovirus, Herpes virus, or Rabies virus. The skilled person is able to make the appropriate selection and adaptation for a specific target animal.

For the construction of an LRCM the well-known technique of in vitro homologous recombination can be used to stably introduce an isolated nucleic acid molecule according to the invention into the genome of an LRCM. Alternatively an isolated nucleic acid molecule according to the invention can also be introduced extra-chromosomally into an LRCM, to allow for transient- or episomal expression.

As described above, the preferred utility of the embodiments of the present invention is in veterinary medical use, in particular for vaccination against FMD.

As is well known in the art, FMDV capsids that are more stable in vitro will also provide an improved humoral immune response upon use as a vaccine. The reason being that there are more intact capsids in the sample; effectively this results in a higher dose of an antigen of improved immunogenic quality.

However, for confirmation, and to illustrate the advantageous utilities of the invention, a number of in vivo experiments were done using VP2 protein mutant-containing FMDV capsids, either as empty- or as virion capsids that were formulated into an FMD vaccine, and used for animal vaccinations. Details are described hereafter.

An FMD vaccine prepared from a similar SAT-2 serotype FMDV VP2 protein mutant capsid, was able to induce in guinea pigs—even after storage for 1 month—a virus-neutralising immune response in a significantly larger number of the vaccinates, as compared to that induced by a vaccine of its wildtype SAT-2 parent strain: 10/10 had neutralising levels of antibodies, as compared to only 2/10 of the targets receiving the unsubstituted VP2 protein capsids.

This experiment was repeated with similar mutant- and wildtype SAT-2 vaccines, except that they had now been stored for 6 months. Guinea pigs were vaccinated, and tested for seroconversion at 12 days post-vaccination. The serology showed that no guinea pig receiving the wildtype VP2 protein containing capsid vaccine seroconverted, whereas 6/10 guinea pigs receiving the VP2 protein mutant-containing capsid vaccine had significant levels of virus neutralising antibodies. See Examples for details and results.

Therefore, in a further aspect, the invention relates to an FMDV VP2 protein mutant, an FMDV capsid, an isolated nucleic acid molecule, a host cell, and/or an LRCM, all according to the invention, for use as a vaccine against FMD.

In a further aspect, the invention relates to an FMDV VP2 protein mutant, an FMDV capsid, an isolated nucleic acid molecule, a host cell, and/or an LRCM, all according to the invention, for the vaccination against FMD.

In a further aspect the invention relates to a vaccine against FMD comprising an FMDV VP2 protein mutant, an FMDV capsid, an isolated nucleic acid molecule, a host cell, and/or an LRCM, all according to the invention, and a pharmaceutically acceptable carrier.

In a further aspect the invention relates to the use of an FMDV VP2 protein mutant, an FMDV capsid, an isolated nucleic acid molecule, a host cell, and/or an LRCM, all according to the invention, for the manufacture of a vaccine against FMD.

A "vaccine" induces in a target animal an immune response that aids in preventing, ameliorating, reducing sensitivity for, or treatment of a disease or disorder resulting from infection with a micro-organism. The vaccine-induced protection is achieved as a result of administering at least one antigenic molecule derived from that micro-organism. This will cause the target to show a reduction in the number, or the intensity, of clinical signs caused by the micro-organism. This may be the result of a reduced invasion, or infection rate by the micro-organism, leading to a reduction in the number or the severity of lesions and effects that are caused by the micro-organism, or by the target's response thereto.

The term "vaccine" implies the use of an immunologically effective amount of an antigenic compound, and the presence of a pharmaceutically acceptable carrier. The antigenic compounds for the invention are an FMDV VP2 protein mutant, an FMDV capsid, a host cell, and/or an LRCM, all according to the invention.

In the case of an isolated nucleic acid molecule according to the invention, this nucleic acid is not an antigen itself, but will produce an antigen when expressed under appropriate conditions.

What constitutes an immunologically effective amount for the vaccine against FMD according to the invention is dependent on the desired effect and on the specific characteristics of the vaccine that is being used. Determination of the effective amount is well within the skills of the routine practitioner, for instance by monitoring the immunological response following vaccination, or after a challenge infection, e.g. by monitoring the targets' clinical signs of disease, serological parameters, or by re-isolation of the pathogen, and comparing these to responses seen in mock vaccinated animals.

The efficacy of a vaccine according to the invention becomes apparent upon comparing a vaccinated and a mock vaccinated target animal. Methods to assess such vaccine efficacy are well known in the art.

"FMD" is a disease that is characterised by well-known symptoms, and can be diagnosed by a variety of diagnostic or microbiological techniques, all well-known in the art.

The skilled person can readily observe the difference that the vaccine against FMD according to the invention makes to the level of clinical signs of FMD to a target animal, by monitoring the symptoms of disease normally caused by FMDV, e.g. as expressed in a clinical score, so that the effect of vaccination on clinical scores of vaccinated and mock vaccinated target animals upon infection can then be compared.

A "pharmaceutically acceptable carrier" aids in the effective administration of an active vaccine compound, without causing (severe) adverse effects to the health of the target animal to which it is administered. Such a carrier can for instance be sterile water or a sterile physiological salt solution. In a more complex form the carrier can e.g. be a buffer, which can comprise further additives, such as stabilisers or preservatives. Details and examples are for instance described in well-known handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

A further advantageous effect of vaccination as described for the invention is the prevention or reduction of the spread of FMDV in a geographical area or in a population, the so-called horizontal spread of infection. Consequently, this leads to a reduction of the prevalence of FMDV. In this embodiment the vaccine blocks, or at least reduces FMDV transmission.

Therefore in a preferred embodiment, the vaccine against FMD according to the invention can be used for reducing the prevalence of FMDV in a geographical area.

The vaccine against FMD according to the invention, when containing a nucleic acid molecule according to the invention in DNA form, is effectively a so-called DNA vaccine'. In such an embodiment, a DNA molecule is introduced into a target animal; when it is taken up into cells, it is expressed, and resulting protein is presented to the target's immune system generating an immune response. In this case the protein expressed is preferably an FMDV empty capsid according to the invention. The DNA vaccine can be introduced in a variety of ways, and can be in different forms, either as naked or as modified DNA, or attached to or encapsulated by a carrier, for example gold-particles.

Direct vaccination with DNA has been successful for many different proteins, as reviewed in e.g. Donnelly et al. (1993, The Immunologist, vol. 2, p. 20-26). For FMDV, see Kim et al. (2006, J. of Gene Med., vol. 8, p. 1182).

Although an FMDV capsid according to the invention has an enhanced biophysical stability, the vaccine against FMD according to the invention may comprise a stabiliser, e.g. to protect sensitive components from being degraded, to enhance the shelf-life of the vaccine, and/or to improve freeze-drying efficiency. Generally stabilisers are large molecules of high molecular weight, such as lipids, carbohydrates, or proteins; for instance milk-powder, gelatine, serum albumin, sorbitol, trehalose, spermidine, Dextrane or polyvinyl pyrrolidone, and buffers, such as alkali metal phosphates.

Preferably the stabiliser is free of compounds of animal origin, or even: chemically defined, as disclosed in WO 2006/094,974.

Also preservatives may be added, such as thimerosal, merthiolate, phenolic compounds, and/or gentamicin.

It goes without saying that admixing other compounds, such as carriers, diluents, emulsions, and the like to vaccines according to the invention are also within the scope of the invention. Such additives are described in well-known handbooks such as: "Remington", and "Veterinary Vaccinology" (both supra).

For reasons of e.g. stability or economy, the vaccine against FMD according to the invention may be freeze-dried. In general this will enable prolonged storage at temperatures above zero ° C., e.g. at 4° C.

Procedures for freeze-drying are known to persons skilled in the art, and equipment for freeze-drying at different scales is available commercially.

Therefore, in a more preferred embodiment, the vaccine against FMD according to the invention is characterised in that the vaccine is in a freeze-dried form.

To reconstitute a freeze-dried vaccine composition, it is suspended in a physiologically acceptable diluent. This is commonly done immediately before use, to ascertain the best quality of the vaccine. The diluent can e.g. be sterile water, or a physiological salt solution. The diluent to be used for reconstituting the vaccine can itself contain additional compounds, such as an adjuvant. In another embodiment the freeze dried vaccine may be suspended in an emulsion as outlined in EP 382.271

In a further embodiment of the freeze dried vaccine according to the invention, the diluent for the vaccine is supplied separately from the freeze dried cake comprising the rest of the vaccine, and is preferably a buffered diluent. In this case, the freeze dried vaccine and the diluent composition form a kit of parts that together embody the present invention.

Therefore, in a preferred embodiment of the freeze dried vaccine against FMD according to the invention, the vaccine is comprised in a kit of parts with at least two types of containers, one container comprising the freeze dried vaccine, and one container comprising an aqueous diluent.

The vaccine against FMD according to the invention may additionally comprise a so-called "vehicle"; this is a compound to which the proteins, nucleic acids, host cells and/or LRCMs all according to the invention adhere, without being covalently bound to it. Such vehicles are i.a. bio-microcapsules, micro-alginates, liposomes, macrosols, aluminium-hydroxide, phosphate, sulphate or -oxide, silica, Kaolin™ and Bentonite™, all known in the art.

An example is a vehicle in which the antigen is partially embedded in an immune-stimulating complex, the so-called ISCOM™ (EP 109.942, EP 180.564, EP 242.380).

In addition, the vaccine against FMD according to the invention may comprise one or more suitable surface-active compounds or emulsifiers, e.g. a component from the Span™ or Tween™ family.

Target for the vaccine against FMD according to the invention evidently are animals that are susceptible to infection with FMDV, as described above. However, the age, weight, sex, immunological status, and other parameters of the target animal to be vaccinated are not critical. However it is evidently favourable to vaccinate healthy targets, and to vaccinate as early as possible to prevent any field infection. Target animals for the vaccine against FMD according to the invention may be seropositive or -negative for FMDV or for antibodies to FMDV. As an infection by FMDV can be established already at young age, therefore the vaccine against FMD according to the invention can be applied within the first 2 weeks after birth; however the presence of maternally derived antibodies may need to be factored in for an efficient vaccination at young age.

The vaccine against FMD according to the invention can equally be used as prophylactic and as therapeutic treatment, and interferes both with the establishment and/or with the progression of an FMDV infection or its clinical signs of disease.

The vaccine against FMD according to the invention can effectively serve as a priming vaccination, which can later be followed and amplified by a booster vaccination, with either the same vaccine according to the invention, or with an inactivated whole FMDV virus vaccine.

The scheme of the application of the vaccine against FMD according to the invention to the target animal can be in single or in multiple doses, which may be given at the same time or sequentially, in a manner compatible with the required dosage and formulation, and in such an amount as will be immunologically effective for the target animal.

The protocol for the administration of the vaccine against FMD according to the invention ideally is integrated into existing vaccination schedules of other vaccines for that target animal.

In areas where FMD vaccination is common, the standard procedure is to revaccinate at 6 month intervals. Therefore the vaccine against FMD according to the invention is advantageously applied in a semi-annual dose.

The vaccine against FMD according to the invention can be administered in doses containing between 0.1 and 1000 μg of an FMDV capsid according to the invention. Smaller or larger doses can in principle be used; preferably a vaccine dose contains between 10 and 1000 μg of an FMDV capsid according to the invention.

The vaccine against FMD according to the invention, can be administered in a volume that is acceptable for the target animal, for instance, one vaccine dose can be between 0.1 and 10 ml. Preferably the volume of one dose is between 0.25 and 5 ml.

The vaccine against FMD according to the invention can be administered to the target animal according to methods known in the art. Preferred application is by parenteral route, such as through all routes of injection into or through the skin: e.g. intramuscular, intravenous, intraperitoneal, intradermal, submucosal, or subcutaneous.

It goes without saying that the optimal route of application will depend on the specific vaccine formulation that is used, and on particular characteristics of the target animal.

The preferred application route for the vaccine against FMD according to the invention is by intramuscular or by subcutaneous injection.

The vaccine against FMD according to the invention can advantageously be used as a marker vaccine, when the vaccine is based on an FMDV empty capsid according to the invention. A marker vaccine is known as a vaccine that allows the discrimination between vaccinated and infected subjects (the so-called: DIVA principle). The differentiation can e.g. be made by detection of a marker vaccine-characteristic antibody spectrum that is different from the antibody spectrum induced by infection with the wild type infectious agent. For the present invention this difference can for instance be made in respect of antibodies against FMDV non-structural proteins; such antibodies would develop in case of infection with a replicating FMDV virion, but not upon inoculation with an empty capsid. This can conveniently be detected by a serological assay such as an ELISA or immuno-fluorescence assay.

Therefore, in a preferred embodiment, the vaccine against FMD according to the invention is a marker vaccine.

It is well within the reach of a skilled person to further optimise the vaccine against FMD according to the invention. Generally this involves the fine-tuning of the efficacy of the vaccine, so that it provides sufficient immune-protection. This can be done by adapting the vaccine dose, volume, or antigen content; by using the vaccine in another form or formulation; by adapting the other constituents of the vaccine (e.g. the stabiliser or the adjuvant); or by application via a different route.

The vaccine against FMD according to the invention may additionally comprise other compounds, such as an adjuvant, an additional antigen, a cytokine, etc. Alternatively, the vaccine against FMD according to the invention can advantageously be combined with a pharmaceutical component such as an antibiotic, a hormone, or an anti-inflammatory drug.

In a preferred embodiment, the vaccine against FMD according to the invention is characterised in that it comprises an adjuvant.

An "adjuvant" is a well-known vaccine ingredient, which in general is a substance that stimulates the immune response of the target in a non-specific manner. Many different adjuvants are known in the art. Examples of adjuvants are: Freund's Complete and -Incomplete adjuvant, vitamin E, non-ionic block polymers and polyamines such as dextran sulphate, carbopol and pyran, aluminium compounds such as Alum-phosphate or Alum-hydroxide, Saponin, preferably QuilA™, etc.

Furthermore, peptides such as muramyldipeptides, dimethylglycine, tuftsin, are often used as adjuvant, and mineral oil e.g. BAYOL™ or MARKOL™, MONTANIDE™ or light paraffin oil, vegetable oils or combination products such as ISA™ from SEPPIC™, a water-in-oil-in-water formulation, or DILUVACFORTE™, a dl-tocopheryl acetate adjuvant can advantageously be used. An emulsion can be e.g. a water-in oil (w/o), oil-in water (o/w), water-in-oil-in-water (w/o/w), or a double oil-emulsion (DOE).

Preferred adjuvant for the vaccine against FMD according to the invention is an adjuvant comprising an alum composition, or an oil-emulsion. More preferred is the combination of an alum component and an oil-emulsion.

It goes without saying that other ways of adjuvating, adding vehicle compounds or diluents, emulsifying or stabilizing a vaccine are also within the scope of the invention. Such additions are for instance described in the well-known handbooks.

The vaccine against FMD according to the invention can advantageously be combined with another antigen.

Therefore, in a more preferred embodiment the vaccine against FMD according to the invention is a combination vaccine, comprising an additional immunoactive component.

The "additional immunoactive component" may be an antigen, an immune enhancing substance, and/or a vaccine; either of these may comprise an adjuvant.

The additional immunoactive component when in the form of an antigen may consist of any antigenic component of veterinary importance. It may for instance comprise a biologic or synthetic molecule such as a protein, a carbohydrate, a lipopolysacharide, or a nucleic acid molecule encoding a proteinaceous antigen. Also a host cell comprising such a nucleic acid, or an LRCM containing such a nucleic acid molecule, may be a way to deliver a nucleic acid molecule or the additional immunoactive component. Alternatively it may comprise a fractionated or killed microorganism such as a parasite, bacterium or virus, or a subunit of any of these.

The additional immunoactive component(s) may be in the form of an immune enhancing substance e.g. a chemokine, or an immunostimulatory nucleic acid comprising a CpG motif. Alternatively, the vaccine against FMD according to the invention may itself be added to a vaccine.

In a preferred embodiment, the vaccine according to the invention can be a combination of one or more VP2 protein mutant, an FMDV capsid and/or a vaccine, all according to the invention, to allow for an effective immune protection against a certain FMDV serotype.

In a further preferred embodiment, the vaccine according to the invention can be a combination of one or more VP2 protein mutant, an FMDV capsid and/or a vaccine, all according to the invention, that derive from different FMDV serotypes, in order to provide an effective and broad immune protection against more than one FMDV serotype.

In a further preferred embodiment, the vaccine according to the invention can be combined with an FMDV vaccine that is not a vaccine according to the invention, such as an inactivated FMDV- or an FMDV subunit vaccine, to form a broad combination vaccine against FMD.

In a further preferred embodiment, the FMD vaccine according to the invention comprises antigens from more than one FMDV serotype; more preferably the FMD vaccine is multivalent in that it protects against more than one variant from a certain FMDV serotype, whereby the actual combination of antigens is determined by the prevalence in a geographical area.

In a preferred embodiment, the combination vaccine according to the invention is characterised in that the additional immunoactive component or nucleic acid molecule encoding the additional immunoactive component is, or is obtained from, a micro-organism infective to an animal that is also a target animal for a vaccine against FMD according to the invention.

The advantage of such a combination vaccine according to the invention is that it not only induces an immune response against FMD but also against other pathogens while only a single handling of the animal target for the vaccination is required, thereby preventing needless vaccination-stress to the target animal, as well as reduction of time- and labour costs.

Examples of such additional immunoactive components are in principle all viral, bacterial, and parasitic pathogens amenable to vaccination of an animal that is also a target animal for the vaccine against FMD according to the invention.

For example, for porcines: porcine circovirus, porcine reproductive and respiratory syndrome virus, pseudorabies virus, porcine parvo virus, classical swine fever virus, *Mycoplasma hyopneumoniae, Lawsonia intracellularis, E. coli, Streptococcus, Salmonella, Clostridia, Actinobacillus pleuropneumoniae, Pasteurella, Haemophilus, Erysipelothrix, Bordetella, Toxoplasma, Isospora, Trichinella*, etc.

For bovines: Neospora, Dictyocaulus, Cryptosporidium, Ostertagia, Babesia, Theileria, Anaplasma, Trypanosoma, Cowdria, Toxoplasma, bovine rotavirus, bovine viral diarrhoea virus, bovine coronavirus, bovine infectious rhinotracheitis virus (bovine herpes virus), bovine paramyxovirus, bovine parainfluenza virus, bovine respiratory syncytial virus, rabies virus, bluetongue virus, *Pasteurella haemolytica, E. coli, Salmonella, Staphylococcus, Mycobacterium, Brucella, Clostridia, Mannheimia, Haemophilus, Fusobacterium*, etc.

For ovines or caprines: *Toxoplasma, Neospora, Cowdria, Babesia, Theileria, Anaplasma, Eimeria, Trypanosoma*, peste des petit ruminant virus, bluetongue virus, Schmallenberg virus, *Mycobacterium, Brucella, Clostridia, Coxiella, E. coli, Chlamydia, Clostridia, Pasteurella, Mannheimia*, etc.

A vaccine against FMD according to the invention is prepared by means well known to the skilled person.

Therefore, in a further aspect the invention relates to a method for the preparation of the vaccine against FMD according to the invention, the method comprising the admixing of an FMDV VP2 protein mutant, an FMDV capsid, an isolated nucleic acid molecule, a host cell, and/or an LRCM, all according to the invention, with a pharmaceutically acceptable carrier.

The vaccine against FMD according to the invention can be prepared by methods as described herein, which are readily applicable by a person skilled in the art. For example, an FMDV capsid according to the invention is produced industrially in smaller or larger volumes, either by replication of the virion capsid on appropriate host cells, or by expression of the empty capsid in host cells in an expression system. Such cultures are harvested, either as whole cells or as a cell-lysate.

In the case of infectious FMDV virion capsids, the final product of the in vitro culture will typically first be inactivated. This can be done in several ways, commonly by chemical inactivation, such as with formalin, beta-propiolactone (BPL), binary ethyleneimine (BEI), or beta-ethanolamine (BEA).

A lysate can be produced by physical (French press, sonifier), or chemical (detergents) ways. The suspension may be further purified, or be concentrated, e.g. by centrifugation or filtration. The resulting antigen preparation is then combined with pharmaceutically acceptable excipients, formulated into a vaccine, and filled-out into appropriate sized containers. The various stages of the manufacturing process will be monitored by adequate tests, for instance by immunological tests for the quality and quantity of the antigens; by micro-biological tests for inactivation, sterility, and absence of extraneous agents; and ultimately by studies in animals for vaccine efficacy and safety. All these are well known to a skilled person. After extensive testing for quality, quantity and sterility such vaccine products are released for sale.

General techniques and considerations that apply to the preparation of vaccines are well known in the art and are described for instance in governmental regulations (Pharmacopoeia) and in handbooks such as: "Veterinary vaccinology" and: "Remington" (both supra).

The vaccine against FMD according to the invention may take any form that is suitable for administration to target animals, and that matches the desired route of application and the desired effect.

Preferably the vaccine against FMD according to the invention is formulated in a form suitable for injection, thus an injectable liquid such as a suspension, solution, dispersion, or emulsion. Commonly such vaccines are prepared sterile.

An emulsion for use in the invention can e.g. be w/o, o/w, w/o/w, or DOE.

As described, the vaccine against FMD according to the invention can be applied to appropriate target animals in a variety of ways.

Therefore, in a further aspect the invention relates to a method for the vaccination against FMD of an animal susceptible for FMDV, comprising the step of inoculating the animal with a vaccine against FMD according to the invention.

The invention will now be further described with reference to the following, non-limiting, examples.

EXAMPLES

1. Methods And Materials
1.1. Cells and viruses

Baby hamster kidney (BHK) clone 13 cells (strain 21; ATCC CCL-10) were maintained according to standard procedures. FMDV stocks were amplified and titrated in BHK-21 cells using standard procedures. Cultured BHK-21 cells were also used for RNA transfection and virus recovery. In addition, plaque assays were performed in either IB-RS-2 (Instituto Biologico renal suino) cells or Chinese hamster ovary (CHO) cells (strain K1; ATCC CCL-61), respectively propagated in RPMI medium (Sigma) and Ham's F-12 medium (Invitrogen) supplemented with 10% foetal calf serum (FCS, Delta Bioproducts).

One-step growth kinetic analyses of FMDV virion capsids were carried out in BHK-21 cells. Briefly: BHK-21 cells were infected with the virus for 1 h at an m.o.i. of 2-4 pfu/cell, washed with MBS-buffer (25 mM morpholine-ethanesulfonic acid, 145 mM NaCl, pH 5.5). Following incubation at 37° C. for the indicated time intervals, the infected cells were harvested at 2, 4, 6, 8, 10, 12, 16 and 20 h post-infection (p.i.) and subsequently frozen at −70° C. Virus titres were determined and expressed as plaque forming units per millilitre (pfu/ml).

Isolation of virus after infectious copy cloning was on primary pig kidney (PK) cells, as described in Maree et al. (2010, Virus Res., vol. 153, p. 82). Culture, passage and amplification of wildtype and of recombinant FMD viruses was done on BHK-21 cells; infected or transfected 35 mm BHK-21 cell monolayers were frozen and thawed, and ⅒th of the volume was used to inoculate a fresh BHK-21 monolayer. Following virus adsorption (with periodical rocking for 60 min at 37° C.), virus growth medium (VGM; Eagle's basal medium (BME) with 1 FCS, 1 HEPES and antibiotics) was added, and the culture was incubated for no longer than 48 h at 37° C., after which the infected cells were frozen for subsequent passaging of the viruses.

1.2. Infectious clones of FMDV

The infectious clone technology was used as a convenient way of generating infectious virion capsids comprising a specific VP2 protein mutant. The procedures applied were essentially as described in Rieder et., al. (1994, J. Virol., vol.68, p. 7092). In short:

1.2.1. Construction:

A genome-length cDNA copy of the SAT-2 vaccine strain, ZIM/7/83, was constructed following an exchange-cassette strategy using an FMDV A12 genome-length clone for a template, as described (Rieder et al., 1993, J. of Virol., vol. 67, p. 5139; Van Rensburg et al., 2002, Ann. N Y Acad. Sci., vol. 969, p. 83). This initial construct was used for the transfection of in vitro synthesized RNA transcripts, followed by the recovery of infectious viral particles. This was later optimized to allow direct transfection of BHK-21 cells with DNA, and the exchange of the outer capsid-coding region. This system was used to prepare synthetic RNA or plasmid DNA for transfection of BHK-21 cells, and generation of viable SAT-2 FMDV.

1.2.2. Site-Directed Mutagenesis:

Site-directed mutagenesis of infectious clone plasmids was done using amplicon overlap-extension PCR and site-directed mutagenesis, using the QUICKCHANGE XLII™ mutagenesis kit (for easy modification of nucleotides; Clontech) according to the manufacturer's instructions (Papworth et al., 1996, Strategies, vol. 9, p. 4). Briefly, each of the PCR processes involved the use of two genome-specific overlapping (reverse-complemented) oligonucleotides, to introduce mutations into distinct PCR products. The mutagenic primers were designed to be between 40 and 49 nucleotides in length and encoded the desired mutation with about 15 to 20 nucleotides of overlapping sequence that matched the viral sequence on both sides of the mutation. The PCRs were performed with the PFU ULTRA TAQ™ polymerase high fidelity DNA polymerase) and cycling conditions using: 95° C. for 50 s, 60° C. for 60 s, and 68° C. for 6 min (18 cycles).

The PCR amplicons were cut out with an appropriate restriction enzyme, and used to transfect ultra-competent XL10-Gold™ E. coli cells. Following confirmation of the introduced nucleotide mutations by sequencing, a DNA fragment containing the region encoding the VP2 protein mutant was inserted into a DNA cloning plasmid for further use.

In Vitro RNA Synthesis, Transfection and Virus Recovery

RNA was synthesized from linearized plasmid DNA templates with the MEGASCRIPT™ T7 kit (an ultra-high yield in vitro transcription kit; Ambion). The transcript RNAs were examined by agarose gel electrophoresis to evaluate their integrity and the RNA concentrations were determined spectrophotometrically. BHK-21 cell monolayers, in 35 mm cell culture wells (Nunc™), were transfected with the in vitro-generated RNA using LIPOFECTAMINE2000™ (a cationic liposome formulation; InVitrogen). The transfection medium was removed after 3-5 h. and replaced with viral growth medium, followed by incubation at 37° C. for up to 48 h with a 5% $CO_2$ influx. After one freeze-thaw cycle, the transfection supernatants were used for serial passaging on BHK-21 cells. BHK-21 monolayers in 35 mm cell culture wells were infected using ⅒th of clarified infected supernatants and incubated for 48 h at 37° C. Viruses were subsequently harvested from infected cells by a freeze-thaw cycle and passaged four times on BHK-21 cells, using 10% of the supernatant from the previous passage. Following the recovery of viable (recombinant) viruses, the integrity of the viruses was verified once again with automated sequencing using the ABI PRISM™ BIGDYE Terminator Cycle Sequencing Ready Reaction Kit v3.0 (Perkin Elmer Applied Biosystems). Typically viruses were passaged four times before analysis.

RNA Extraction, cDNA Synthesis, and PCR Amplification.

RNA was extracted from infected cell lysates using either a standard guanidinium-based nucleic acid extraction method or TRIZOL™ reagent (a guanidinium thiocyanate reagent: Life Technologies) according to the manufacturer's instructions and used as template for cDNA synthesis. Viral cDNA was synthesised with SUPERSCRIPT III™ (a reverse transcriptase; Life Technologies), as described in Bastos et al. (2001, Arch. Virol., vol. 146, p. 1537).

1.3. Virus Neutralization Test

The detection of a virus-neutralising antibody response in vaccinated animals was done by using the micro-neutralization test, essentially as described in the OIE Manual of Standards (2009). Reference cattle sera were prepared by two consecutive vaccinations (vaccinated on day 0, boosted on day 28, and bled on day 38) with FMDV that are the same as or equivalent to the virus against which the antibody response was to be detected. IB-RS-2 cells were used as the indicator system in the neutralization test. The end point titre of the serum against homologous and heterologous viruses was calculated as the reciprocal of the last dilution of serum to neutralise 100 TCID50 virus in 50% of the wells. One-way antigenic relationships (R1-values) of wildtype and engineered FMDV viruses relative to the reference sera were calculated and expressed as the ratio between the heterologous/homologous serum titre. All neutralization titre determinations were repeated at least twice.

1.4. Sucrose Density Gradient Purification

Sucrose density gradient separation was used for purification of virion capsids, as well as of empty capsids, and at different stages of production, inactivation, or harvest.

FMDV empty capsids from an expression system, such as from Vaccinia or Baculovirus, were harvested, loaded onto a 15-45% sucrose gradient and spun for 20 h at 22.000 rpm (SW41 rotor, Beckman) at 12° C.

FMDV virion capsids from a cell-culture were harvested, clarified, concentrated with 8% (w/v) PEG 6000 at 4°

C. The precipitate was solubilised in 50 mM HEPES (pH 8.0) with 200 mM NaCl and 1% NP40, and resolved on 10-50% (w/v) sucrose density gradients in HEPES/NaCl by rate zonal centrifugation at 36.000×g for 16 h at 4° C.

Next, each gradient was fractionated, and fractions were analysed spectrophotometrically by measuring the absorbance at 260 nm. Fractions containing 146S virions were quantified based on absorption, and pooled for analysis. The presence of the outer capsid proteins was verified by agar-gel protein-electrophoresis using standard SDS-PAGE protocols, or Western blotting. The integrity of the RNA in virion capsids was verified by RT-PCR and sequencing of the VP1 coding region.

1.5. Baculovirus Expression System

The Baculovirus/insect cell expression system (BVES) was used to express FMDV empty capsids with either parental VP2 or VP2 protein mutant. Procedures were essentially as described in (Porta et al., 2013, J. Virol. Methods, vol. 187, p. 406). In short: Sf9 cells were grown in Insect-XPRESS™ (an insect cell culture media; Lonza) supplemented with 2% FCS and antibiotics at 27.5° C. Transfer vector and AcMNPV bacmid KO1629 (0.5 µg of each) were mixed in the presence of 3 µl FUGENE™ (a nonliposomal transfection reagent; Roche) for 20 min at room temperature and used to transfect Sf9 cells at a density of 1.2×10^6/well in a 6-well plate.

Since Baculovirus DNA with a knockout of gene 1629 will not initiate an infection unless rescued by recombination with a Baculovirus transfer vector, the AcMNPV harvested in the culture supernatant after 5 days was 100% recombinant virus. Virus stocks were produced by infecting Sf9 cell monolayers at a confluence of 70% with 200 µl recombinant virus inoculum per 175 cm² flask and harvested from culture supernatants after 5 days. Alternatively, adherent cell-culture in roller bottles, and 2 l suspension cultures were used. For the expression of empty capsids, Sf9 cells at a density of 1-2 10^6/ml were infected with 1/10 volume of Baculovirus stock. After 3 days virus extraction was with 1% Triton X-100 in the presence of 5 µl/ml protease inhibitor cocktail (Sigma).

1.6. Vaccinia Expression System

The Vaccinia virus expression system was used to express FMDV empty capsids, comprising either wildtype VP2 protein or VP2 protein mutant. Procedures were essentially as described in King et. al. (supra), these have been applied to serotypes O, SAT2 and A. In short the procedures, exemplified by A22 were as follows.

1.6.1. Vaccinia Virus Transfer Vectors

An expression cassette based on the sequence of FMDV A22 Iraq was designed, synthesized de novo (Geneart™) and cloned into the Vaccinia virus transfer vector pBG200 downstream of the T7 promoter. Substitution of a BstEII-SpeI fragment with a sequence encoding the VP2 H93F mutation converted the pBG200-A22-wt plasmid to pBG200-A22-H93F.

1.6.2. Generation and Selection of Vaccinia Virus Recombinants

Recombinant Vaccinia viruses were made by transfecting plasmids pBG200-A22-wt and pBG200-A22-H93F into CV-1 cells infected with Vaccinia virus (VV) strain WR. Recombinant VVs (with an interrupted thymidine kinase gene) were selected in HuTK-143 cells using 5-bromo-2-deoxyuridine. Three rounds of plaque purification in conjunction with screening by PCR using FMDV-specific primers were carried out to obtain stable recombinant VVs. These were amplified in RK13 cells and virus stocks titrated by plaque assay on BS-C-1 cells. All mammalian cells were grown at 37° C. in DMEM, supplemented with 10% FCS and appropriate antibiotics.

1.6.3. Sedimentation of Empty Capsids Produced via Vaccinia Virus Expression A 175 cm² flask of RK13 cells was infected with either vA22-wt or vA22-H93F at an MOI 10 and vTF7.3 at an MOI 5. After 24 h cells were harvested by centrifugation at 2.000×g for 5 min at 4° C. and the pellet resuspended in 1 ml 0.5% IGEPAL™ (a nonionic detergent: Sigma) in 40 mM sodium phosphate, 100 mM NaCl pH 7.6. Samples were incubated on ice for 20 min, clarified, loaded onto a 15-45% sucrose gradient and spun for 20 h at 22.000 rpm (SW41 rotor, Beckman) at 12° C. Each gradient was fractionated into 12 fractions of 1 ml and aliquots were analysed by Western blotting.

1.7. Capsid Dissociation Assays

Wild-type and VP2 protein mutant-containing FMDV capsids, present in cell culture supernatants or in samples that were purified by sucrose gradient, were taken up into standard TNE buffer, and subjected to conditions of different pH or temperature to assess their stability.

1.7.1. pH Stability of Virion Capsids:

Briefly: 10% to 10^7 pfu/ml of infectious FMDV virion capsids were mixed with TNE buffer (pH preferably above 7), at a ratio of 1:50 v/v respectively. The mixtures were subsequently incubated for 30 min. at room temperature. As a control, virus particles were also mixed with virus growth medium at the same ratio. The samples were subsequently neutralised with 1 M Tris (pH 7.4), 150 mM NaCl and titrated on BHK-21 cells. Alternatively, sucrose gradient purified particles with an approximate titre of 4-8×10^6 pfu/ml were treated at pH 6.0, for different time intervals following a 1:50 dilution in TNE buffer.

1.7.2. Temperature Stability of Virion Capsids:

Alternatively FMDV virion capsids in TNE buffer (pH 7.4) were treated at temperatures of 25, 37, 45 or 55° C. for 30 minutes in a water bath, after which the samples were cooled on ice and titrated. The 1:50 dilution of the sucrose gradient purified particles ensured that any stabilising effect of the sucrose was negligible. Also, sucrose gradient purified particles with an approximate titre of 4-8×10% pfu/ml were heated to 42° C. or 49° C., for different time intervals.

The number of infectious FMDV virion capsids remaining after low pH- or high temperature treatment was determined by plaque titrations on BHK-21 cells. The respective logarithmic values of the virus titres at the different time points were linearly fitted and the slopes were determined. The percentage of remaining infectious particles was also calculated and plotted along with the exponential decline used to calculate the inactivation rate constant.

1.7.3. Stability Assays of Empty Capsids:

A 200 µl aliquot of an empty capsid-containing fraction was diluted 1:3 either (i) with phosphate buffer pH 7.6 and incubated in a water bath at 56° C. for 2 h, or (ii) with 50 mM sodium acetate buffer pH 4.6, to give a final pH of 5.2 and incubated at room temperature for 15 min before neutralisation with NaOH. Treated samples were loaded onto 15-45% sucrose gradients, and centrifuged. Each fraction was precipitated with an equal volume of saturated ammonium sulphate overnight at 4° C. Precipitates were collected by centrifugation at 16.000×g for 15 min at 4° C. and analysed by western blot.

1.8. ELISA Assays

ELISA was performed as described in Harmsen et al. (supra). In short this regards a double antibody sandwich ELISA for quantification of FMDV capsids, using one of two single-domain Llama derived antibody fragments that are specific for FMDV structures of either 146S virion capsid (antibody M170) or of 12S pentamer structures (antibody M3). Only O serotype strains could be detected in the 146S specific ELISA, whereas strains of most serotypes are detected in the 12S specific ELISA. However, the 146S concentration of serotypes A and Asia 1 FMDV strains could be measured indirectly using the 12S specific ELISA by prior conversion of 146S into 12S particles by heat treatment. Stability was determined by thermofluor assay.

1.9. Electron Microscopy:

EM was used to study the level of intactness of virion capsids after chemical inactivation, and of empty capsids, after heat treatment.

Purified chemically-inactivated virion capsids of wildtype and VP2 S93Y were examined by electron microscopy after a storage period of 10 days at 4° C. The samples were allowed to adhere on carbon coated formvar grids for 30 s, followed by two washes with water before staining with 1% uranyl acetate for 45 s. Excess stain was removed by blotting and the grids examined on a FEI T12 electron microscope operating at 80 KeV. For empty capsids, purified wildtype and VP2 S93F capsids were heated to 56° C. for 2 hours before examining by EM.

1.10. Thermofluor Assays

The Thermofluor shift assay was performed as described (Walter et al., 2012, supra) to measure and compare temperature stability of infectious FMDV virion capsids; either VP2 protein mutant- or wildtype VP2 protein-comprising FMDV were used to test the capsid stability by detecting the release of the viral RNA, by monitoring the RNA-specific fluorescent dye SYBR GREEN™. A temperature gradient was applied from 25-95° C. and viral genome release was detected by increase in fluorescence as the capsids dissociated into pentamers.

1.11. FMDV Inactivation

Mutant and wildtype FMDV were harvested from infected BHK-21 cell monolayers, and were inactivated with 5 mM binary ethyleneimine (BEI) for 26 h at 26° C. Next they were PEG concentrated and purified on a sucrose gradient. The BEI-inactivated, sucrose gradient-purified antigens were used for formulation into vaccines for animal vaccinations.

1.12. Animal Vaccination Experiments

Vaccines prepared from FMDV capsids were tested in the standard FMDV serology model: the Guinea pig, to evaluate their immunogenic potency and duration of the antibody response, as a function of their antigen stability. Vaccine antigens were either wildtype FMDV capsids, or VP2 S93Y substitution mutant-comprising capsids of the wildtype strain. These were tested both as inactivated virion capsids and as empty capsids, and were tested either for SAT-2 serotype or for O serotype, respectively. All animal experiments were performed in full compliance with legal- and animal welfare regulations. Groups of 10 Guinea pigs received a 0.2 ml dose of a test- or control vaccine by intra-muscular inoculation, and were bled at day zero and at different time points during the course of the experiment. FMDV-neutralizing antibodies in the sera were analysed using the virus neutralisation (VN) test according to OIE guidelines.

2. Results and Conclusions

2.1. Temperature Stability Assays

2.1.1. Stability of Infectious Virion Capsids:

Dissociation Kinetics:

Infectious virion capsids were subjected to dissociation kinetics assays, comparing wildtype- and VP2 protein mutant-containing virion capsids. Virion capsids of both types at a titre of about $2\text{-}10\times10^5$ pfu/ml were incubated at 49° C. for 2 hours. The number of infectious particles remaining intact after this treatment was determined. The temperature inactivation profiles of the particles followed linear kinetics and the lability of the different viruses was reflected by the inactivation rate constant values found; these were: wildtype SAT-2: 0.0155/min.; SAT-2 VP3 E198A: 0.0163/min.; and SAT-2 VP2 S93Y: 0.0075/min.

This showed that the inactivation rate of wildtype and of a (control) VP3 substitution mutant were essentially the same, whereas the inactivation rate for the VP2 S93Y mutant was significantly lower. This reflects the improved thermal stability of FMDV capsids comprising the VP2 protein mutant according to the invention, when compared to capsids with wildtype VP2 protein, or capsids containing VP2 protein with arbitrary substitutions.

When the percentage of infectious FMDV virion capsids remaining after heat treatment was determined, it was found that about 15% of the SAT-2 VP2 S93Y virion capsids remained following a 2 hour incubation at 49° C., compared to only 1.4% remaining of the wildtype SAT-2 and the SAT-2 VP3 E198A substitution mutant virus.

Thermofluor Assays:

The thermofluor shift assay was used as a direct measurement of FMDV capsid stability, in response to temperature variation. The assay detects the release of RNA, monitored by an RNA-specific fluorescent dye that binds the viral genome, upon the dissociation of a capsid. The virions were purified by sucrose gradient, and inactivated with BEI. Virion samples had concentrations between 140 and 420 µg/ml. As a control, FMDV serotype A, isolate 24 virus was included.

Figure 4:
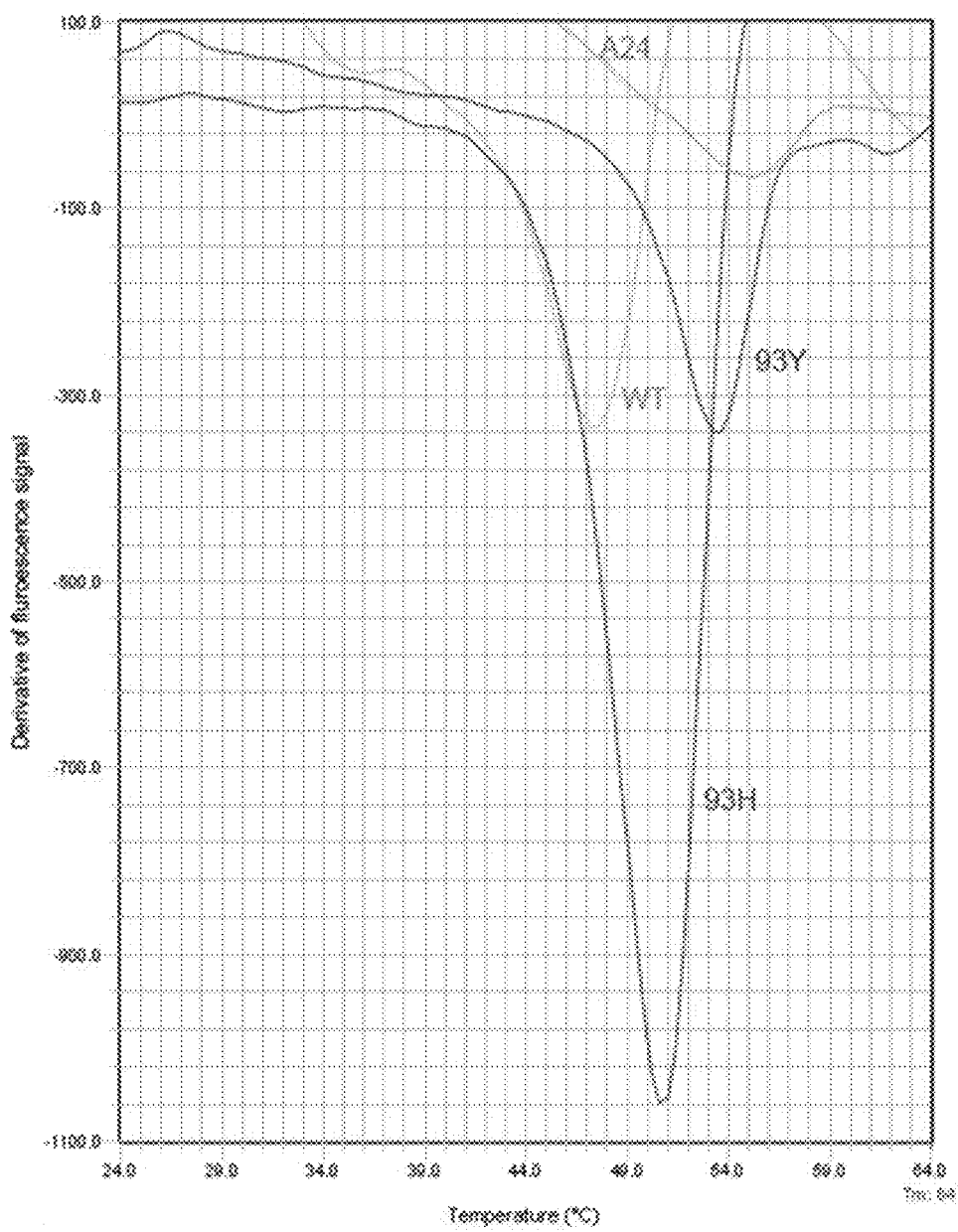

Because typically sharp clear peaks in the first derivative of fluorescence were observed under steady heating, the peak temperatures were taken as a direct indicator of the dissociation temperature for that virus construct. The values found were: SAT-2 VP2 S93Y dissociated at 53° C., SAT-2 VP2 S93H at 51° C., and the wildtype SAT-2 at 47° C., see FIG. 4.

Control samples were: FMDV A24 virus, which had the overall highest dissociation temperature of 55° C., however this is only 2 degrees higher than the SAT-2 VP2 S93Y mutant. A SAT-2 VP2 S113G substitution-mutant virion capsid (not presented in FIG. 4) served as a negative control. This showed a decrease in dissociation temperature to 45° C., even a few degrees lower than the wildtype SAT-2 virus.

The virion capsid SAT-2 VP2 S93Y therefore had the highest increase in dissociation temperature as compared to its wildtype virus of 6° C. This agrees well with the degree of stabilisation observed in the heat inactivation kinetic assay (supra).

Figure 10:
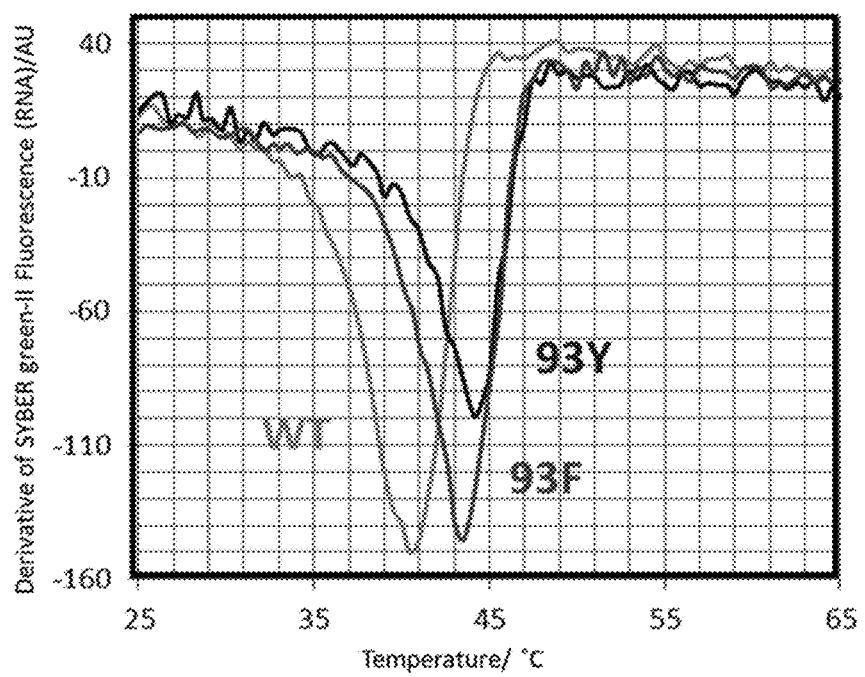
Figure 10:
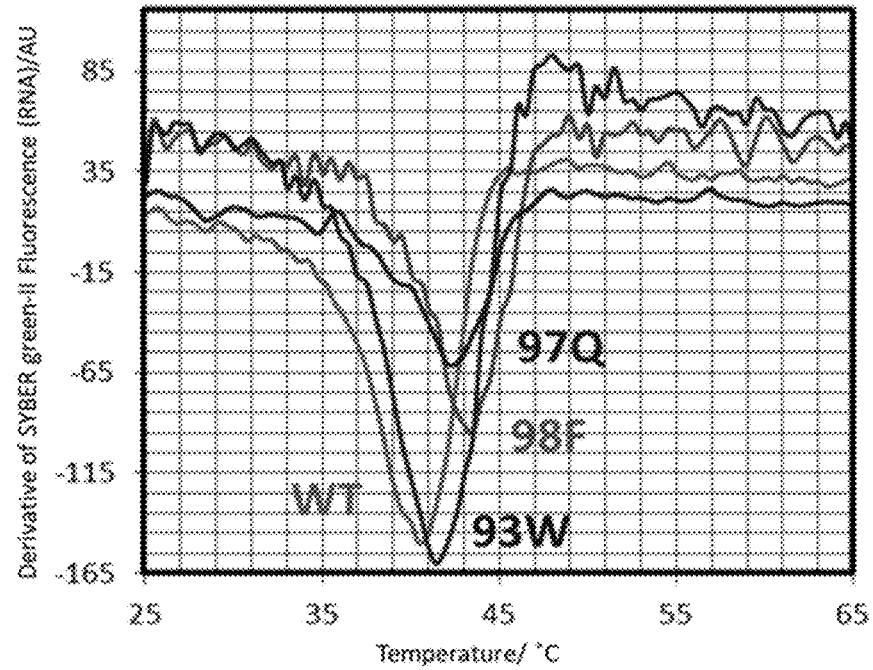

The stability of FMDV virion capsids of serotype O, isolate O1 Manisa was also determined using thermofluor analyses. These assays were run in a different buffer at pH 7.0, therefore their base level differs from that of FIG. 4. Results are presented in FIG. 10, divided over two panels, to prevent cluttering the image. The peak values found were:

Panel A: wt O1M: 40° C.; 93F: 43° C.; 93Y: 44° C.
Panel B: wt O1M: 40° C.; 93W: 42° C.; 97Q: 42° C.; 98F: 44° C.

2.1.2. Stability of Empty Capsids:

Stability of FMDV empty capsids was tested in a variety of ways. First, the sucrose gradient purification already provided a reliable indication of capsid integrity: when capsids had disintegrated, no clear band could be obtained using sucrose gradient centrifugation.

Next, thermostability was tested using gel-electrophoresis and Western blot: sucrose gradient purified empty capsids were heated to 45° C. for 1 h (FIG. 5, panel A), or to 56° C. for 2 h (FIG. 5, panel B). Next, samples were loaded onto a further 15-45% sucrose density gradient, centrifuged, and the gradient was collected into 12 fractions of 1 ml. From each fraction 500 μl was precipitated with 500 μl saturated ammonium-sulphate and the pellet was run on an SDS gel. Finally the gel was blotted and the blot incubated with an antibody against VP1.

Empty capsids that remained intact after heat incubation gathered just below the middle of the sucrose gradient, ending up in fractions 4 and 5, and showed up in the gel-lanes corresponding to these fractions. Whereas (partly) disassembled capsids were less dense and remained near the top of the gradient, and were found in the gel-lanes corresponding to fractions 10 and 11.

Results showed that empty capsids from wildtype FMDV of serotype O, subtype 1 Manisa rapidly disintegrated, and were found in fractions 10-11 for both temperatures. Surprisingly, VP2 protein mutant-containing capsids could much better resist the heat treatment: FMDV capsids with VP2 protein mutants with substitutions S93H and S93F were all totally intact after 1 h at 45° C. (FIG. 5, panel A). After 2 hours at 56° C. the mutant S93H was not stable (all material in fractions 10-11; FIG. 5, panel B); mutant S93Y was partly stable (about 10% was in fraction 10, rest in fraction 4); and S93F was completely stable (all in fraction 4).

Figure 6:
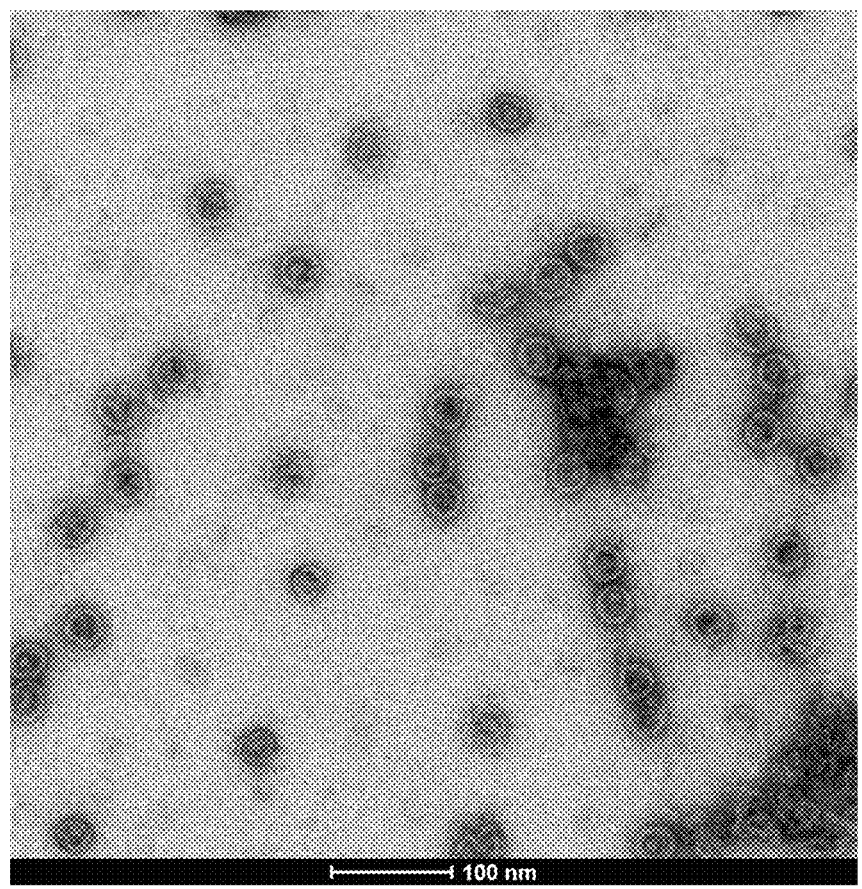

A sample from the VP2 S93F protein mutant comprising empty capsid material from the 2 h 56° C. treatment, was also studied by electron microscopy, which confirmed the gel-electrophoresis results: all these capsids were found to be intact and no pentamers could be seen (FIG. 6, see below).

When FMDV empty capsids of serotype O, isolate O1 Manisa, were expressed via the baculovirus-/insect cell expression system, wildtype O1M empty capsids could not be obtained after the standard 5 day culturing conditions. However a mutant VP2 protein-containing empty capsid, having the S93F substitution could be produced in either roller bottles, or in 2 l. suspension cultures. This yielded adequate amounts of stabilised mutant capsids for analyses such as Western blot, sucrose gradient, ELISA, and EM, as well as for vaccination studies in Guinea pigs.

2.2. ELISA Assays

Figure 7:
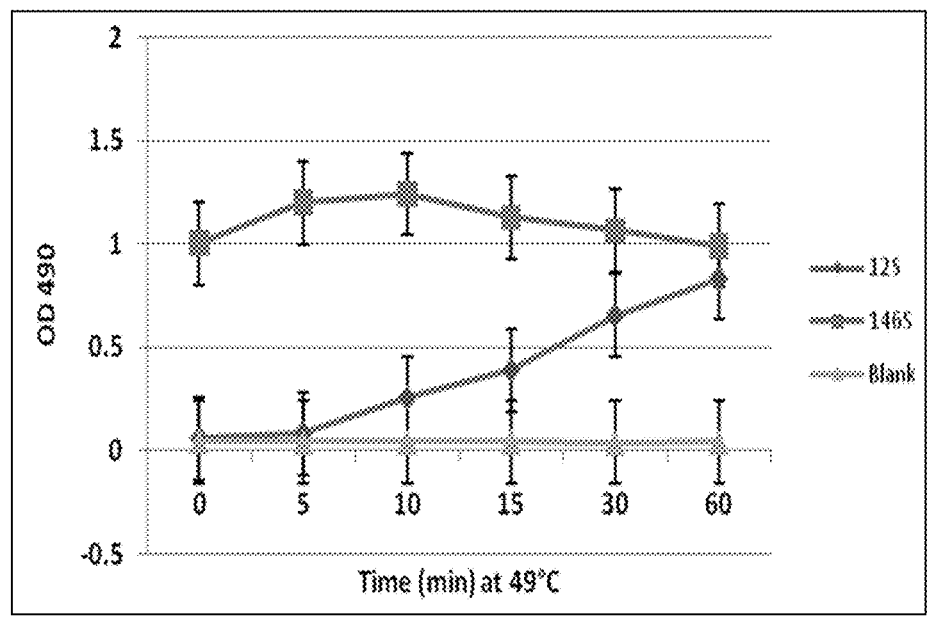
Figure 7:
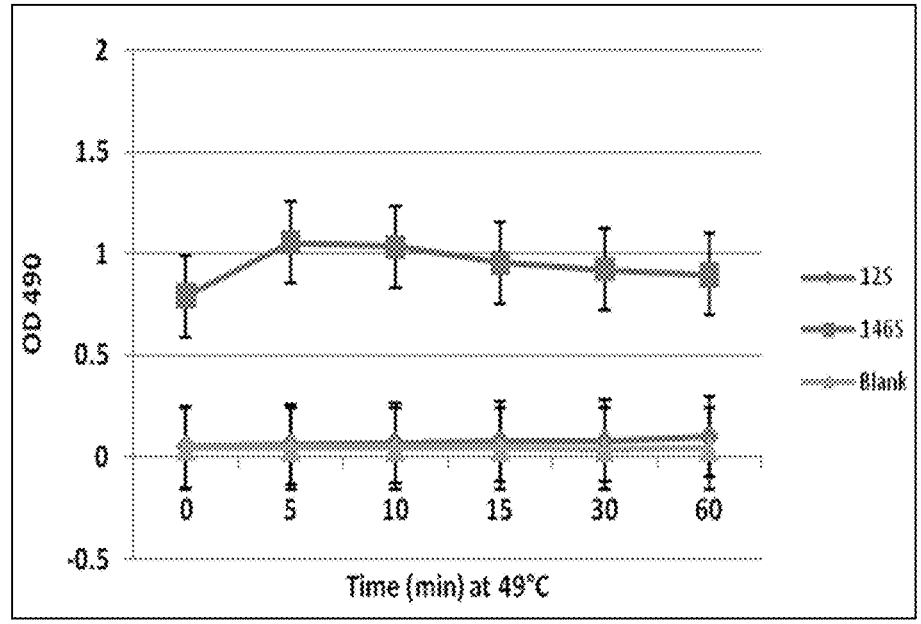

ELISA assays were used to detect the level of dissociation of live infectious FMDV during incubation at 49° C. for 1 hour. Compared were wildtype serotype 0 FMDV (FIG. 7, panel A), and a VP2 protein mutant-containing serotype O FMDV, namely VP2 S93Y (FIG. 7, panel B). The lines correspond to the total amounts of 146S or 12S particles that were detected over time, next to a blank control sample. More 12S signal indicates higher capsid breakdown.

For the wildtype FMDV, virion capsid levels decreased, and 12S levels steadily increased during the 1 h incubation. The blank sample remained at threshold level as expected. However for the VP2 protein mutant-containing virion capsids, no rise in the level of 12S particles was detected, indicating a much improved thermal stability as compared to the wildtype virion capsids.

2.3. Stability After Chemical Inactivation

FMDV virion capsids were subjected to standard chemical inactivation with BEI and analysed by electron microscopy. This was done either directly after the chemical inactivation, or after a further 10 days storage at 4° C. The FMDV capsids tested were either wildtype FMDV of serotype O subtype 1 Manisa, or the corresponding VP2 protein mutant-containing virion capsids with substitution VP2 S93Y.

Figure 8:
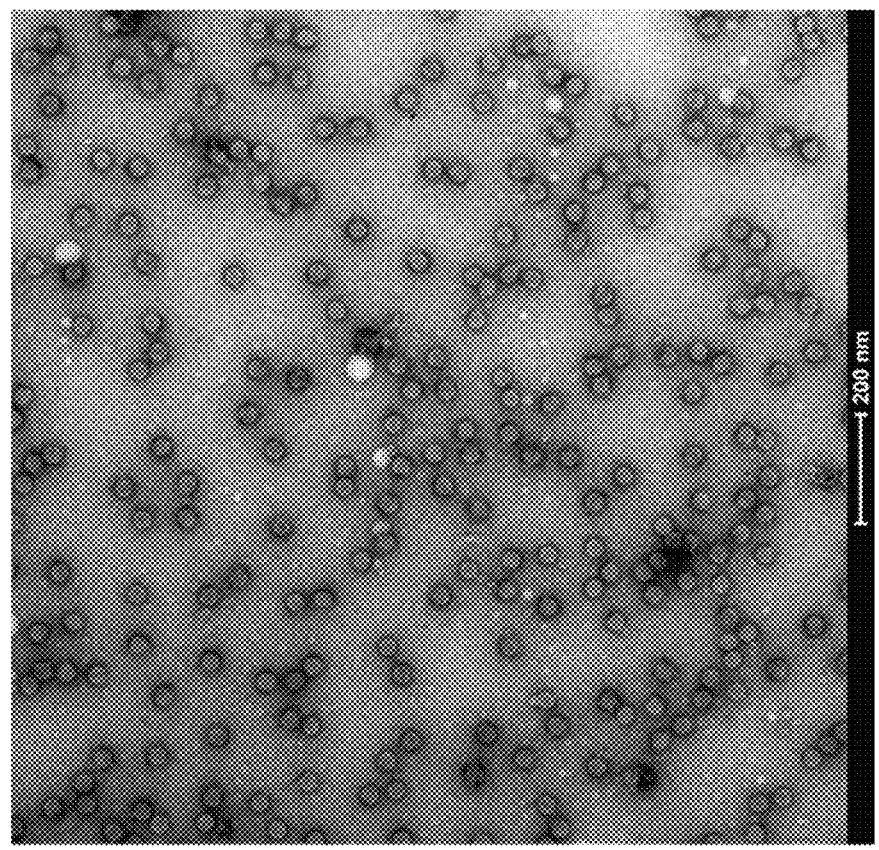
Figure 8:
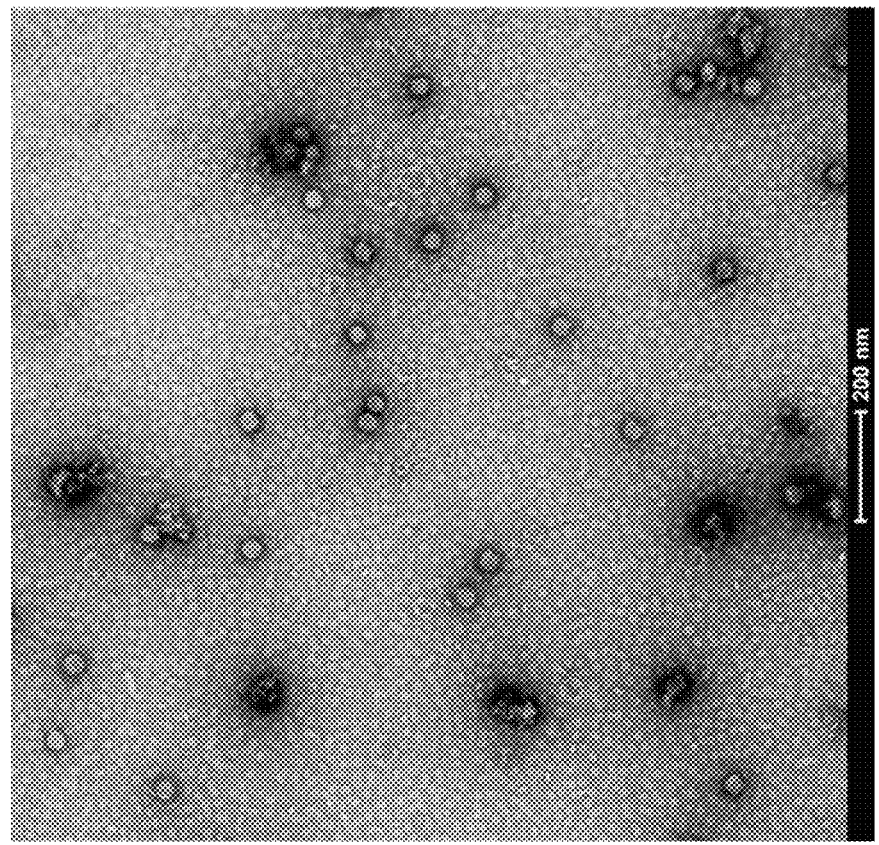

The EM analyses showed that initially the amount of pentamers versus the amount of intact virion capsids was 10:90% for the wildtype virion capsids, and 0:100% for the VP2 protein mutant-containing capsids. After cold storage the difference became much larger; the wildtype material was 80:20% pentamers versus intact virion capsids (FIG. 8, panel A), as compared to 10:90% for the mutant VP2-containing virion capsids (FIG. 8, panel B).

2.4. Results From Animal Vaccination Studies 2.4.1. Vaccination with Empty Capsids:

FMDV empty capsids of Serotype O, subtype 1 Manisa, were expressed in a Baculovirus/insect cell system; empty capsids were either of wildtype, or comprised VP2 protein mutant with the VP2 S93F substitution. Unfortunately, the parental serotype O1 M empty capsids were so unstable they could hardly be detected after insect cell expression (5 days at 27° C., using standard pH 6.5 insect cell culture medium). Therefore only VP2 protein mutant-containing empty capsids were used to vaccinate Guinea pigs. The capsid antigen was formulated in standard w/o/w emulsion, in doses equivalent to 5 or 20 μg 146S antigen per final vaccine dose. As a control, standard inactivated whole virus FMDV vaccine of type O1M was also inoculated.

Virus neutralisation results at 3 and at 4 weeks post vaccination showed Guinea pig VN titres resulting from the S93Y mutant empty capsid vaccine was comparable to the titres obtained with classical FMDV vaccine. It was concluded that the potency of a vaccine based on in vitro expressed VP2 protein mutant-comprising FMDV empty capsids, had demonstrated proof of concept.

2.4.2. Vaccination with Inactivated Virion Capsids:

Virion capsids of FMDV SAT-2 serotype from wildtype and from VP2 protein mutant-comprising virion capsids, carrying the VP2 S93Y substitution, were tested in Guinea pigs. Virion capsids had been inactivated with BEI. First the amount of intact virion capsid antigen was determined, and samples were diluted such that the final vaccine concentration was 5 μg/ml. Samples were formulated in standard w/o/w emulsion, and after formulation, the samples were stored for 1 month at 4° C. Two groups of 10 guinea pigs were immunised, and blood samples were taken at day zero, and at 1 and 6 months post-immunisation. IB-RS-2 cells were used as an indicator system and wildtype FMDV SAT-2/ZIM/7/83 was used as the reference virus. In this set-up Log 2 virus neutralisation titres of 5 and above are considered protective.

Figure 9:
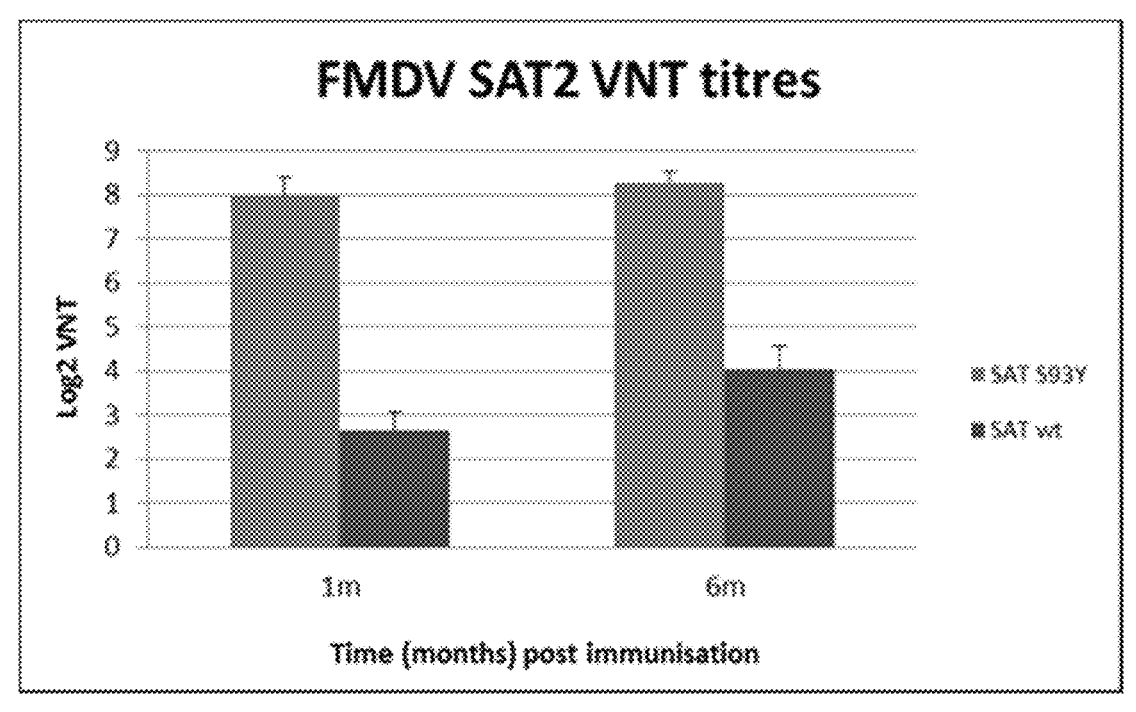

No FMDV neutralising antibodies were detectable on the day of inoculation. The vaccinates receiving the wildtype FMDV virion capsids did not seroresponse above protective levels, whereas all animals receiving virion capsids with the VP2 protein mutant showed protective level of seroresponse, both at 1 and at 6 months post vaccination. The difference in group mean neutralising antibody titres was significant (p>0.05) at both time points (error bars=SEM). Results are presented in FIG. 9.

The fact that the vaccine of the wildtype FMDV virion capsids did not induce a protective seroresponse, was most likely caused by the instability of the native capsids after inactivation, and following the 1 month storage.

However, the virion capsids comprising the VP2 protein mutant according to the invention were so stable they survived both the chemical inactivation and the storage, and still were able to induce solid protective humoral immunity, even after only a single vaccination, and even up to 6 months post vaccination. The inventors were surprised to find this was even possible for an FMDV vaccine of the SAT-2 serotype.

3. Ongoing and Planned Experiments:

3.1. Guinea Pig Vaccination Experiments

A Guinea pig vaccination experiment is in preparation which will use a vaccine of FMDV empty capsids of serotype O1 Manisa, containing either parental empty capsids, or comprising the VP2 protein mutant with the VP2 S93Y substitution. Several test and control groups will be included; groups of 5 Guinea pigs each will receive the different capsid antigens (wildtype or mutant), formulated in a w/o emulsion adjuvated with light mineral oil.

Further, a similar Guinea pig experiment is planned for testing a different adjuvant formulation: FMDV capsids of serotype O and possibly A will be formulated into a single oil-in-water emulsion, using a light paraffin oil.

3.2. Cattle Vaccination-Challenge Studies

Two separate cattle vaccination-challenge studies are planned to be held in appropriate high-containment facilities.

The first study will be a vaccination using inactivated virion capsids of SAT-2 serotype FMDV, with or without VP2 protein mutant VP2 S93Y. According to the protocol non-pregnant heifers will receive a single dose of vaccine, and will be challenged with a wildtype SAT-2 FMDV strain.

We plan to divide 26 cattle into five groups:

Group 1: 6 cattle will be vaccinated with wild type FMDV SAT-2 vaccine in commercial adjuvant;

Group 2: 6 cattle will receive SAT-2 93Y VP2 protein mutant antigen in commercial adjuvant;

Group 3: 6 cattle will receive SAT-2 93H VP2 protein mutant in commercial adjuvant;

Group 4: 6 cattle will receive SAT-2 93H VP2 protein mutant with an alternative adjuvant.

Group 5: 2 cattle receiving a mock vaccination.

Sera will be collected at regular intervals, initially every 2 days, then weekly and monthly, and will be assessed using VN test. Once the VN titres start to drop the animals will be challenged, in conditions of high containment, with $10^4$ cattle adapted, live FMDV viral particles, intradermolingually.

In a comparable experiment, cattle will be vaccinated according to a standard PD50 type protocol, as prescribed by the European Pharmacopeia, using FMDV empty capsids of serotype O1 Manisa, with or without VP2 protein mutant comprising the VP2 S93Y substitution. As control, one group will receive a standard serotype O FMDV vaccine. The protocol incorporates the vaccination, and subsequent challenge infection with a Serotype O wildtype FMDV strain. Experimental analysis will include full serology, as well as challenge virus re-isolation.

LEGEND TO THE FIGURES

FIG. 1:

Schematic structure of the icosahedral FMDV capsid. The VPs are indicated: 1=VP1, 2=VP2, and 3=VP3. A pentamer subunit is outlined by thick lines.

The icosahedral symmetry axes are indicated: 5-fold: pentagon, 3-fold: triangle, and 2-fold: oval. (From: Mateo et al., 2003, J. Biol. Chem., vol. 278, p. 41019, FIG. 1, panel A.)

FIG. 2: Multiple alignment of the amino acid sequence of the VP2 protein αA helix region for a number of representative FMDV isolates; at the top the numbering and the amino acid sequence are indicated from the FMDV serotype O isolate 1 BFS, which is represented in SEQ ID NO: 1 and individually as:

O1BFS SEQ ID NO: 2
O1M 87 SEQ ID NO: 3
CS8c1 SEQ ID NO. 4
ASIA Bar2003 SEQ ID NO: 5
A22 Iraq 95 SEQ ID NO: 6
SAT1 bot SEQ ID NO: 7
SAT ZIM7 83 SEQ ID NO: 8
SAT3 KNP10 90 SEQ ID NO: 9

FIG. 3:

Graphical representation of a 3-dimensional model structure of the two-fold symmetry axis in an FMDV capsid, showing hydrophobic stacking interactions between two neighbouring VP2 protein mutants with a 93W substitution.

FIG. 4:

Illustrative results of a Thermofluor assay, using live FMDV virion capsids from serotype SAT-2. The peaks indicate the temperature at which maximal release of RNA, monitored by RNA-specific fluorescent dye, thus where the FMDV virion capsid fully dissociates. This marks the dissociation temperature.

A24=wildtype FMDV serotype A, isolate 24; 93Y=FMDV SAT-2 VP2 S93Y; 93H=FMDV SAT-2 VP2 S93H; WT=wildtype FMDV SAT-2.

FIG. 5:

Western Blot analysis of heat stable FMDV empty capsids of serotype O, subtype 1 Manisa, which were heated to 45° C. for 1 hour (panel A), or 56° C. for 2 hours (panel B) and then loaded onto a 15-45% sucrose density gradient.

FMDV empty capsids with VP2 S93F or VP2 S93H VP2 protein mutant remained intact at 45° C. (panel A) and migrated through the gradient to fractions 4 and 5 whereas the wild-type VP2 protein containing capsids broke apart on heat treatment, remaining near the top of the gradient in fractions 10 and 11. When the experiment was repeated, empty capsids containing S93F VP2 protein mutant were remarkably stable even after 2 h at 56° C.; VP2 S93Y containing capsids had about 10% degradation, and VP2 S93H containing capsids were unstable.

FIG. 6:

Electron micrograph of heat treated empty FMDV capsids containing VP2 protein mutant with S93F substitution. The mutant capsids were incubated at 56° C. for 2 hours and the samples examined by electron microscopy. The capsids were found completely intact.

Bars indicate a size reference.

FIG. 7:

Results of ELISA assay, detecting the level of dissociation of infectious FMDV virions during incubation at 49° C. for 1 hour. Compared were wildtype serotype O FMDV (panel A), and a VP2 protein mutant-containing serotype O FMDV, namely VP2 S93Y (panel B). The lines correspond to the amounts of 146S or 12S particles that were detected over time, next to a blank control sample.

FIG. 8:

Electron micrographs of chemically inactivated FMDV virion capsids of serotype O subtype 1 Manisa that had been stored after inactivation for 10 days at 4° C. Panel A shows a sample of wildtype FMDV and panel B shows a sample of a similar initial amount of the corresponding virion capsids that comprised a VP2 protein mutant, with substitution S93Y. About 80% of wildtype inactivated capsids were found to be dissociated into pentamers. However inactivated VP2 S93Y mutant capsids were about 90% intact.

FIG. 9:

Graphical representation of results from animal vaccination trial with inactivated SAT-2 FMDV virion capsids comprising VP2 protein mutant with VP2 S93Y substitution. Plotted are the mean Log 2 virus neutralisation titres of groups of 10 Guinea pigs, at 1 month and at 6 months post vaccination. Error bars indicate s.e.m.

The vaccine was based on inactivated SAT2 serotype FMDV virion capsids of either wildtype SAT-2, or VP2 protein mutant-comprising virion capsids with a VP2 S93Y substitution. Log 2 virus neutralisation titres of 5 and above are considered protective. SAT 593Y=SAT-2 VP2 S93Y; SAT wt=wildtype SAT-2.

FIG. 10:

Results of thermofluor analyses with FMDV virion capsids of Serotype O, isolate O1 Manisa. The graphs are divided over two panels, to prevent cluttering the image. These assays were run in a buffer at pH 7.0.

WT=wildtype FMDV serotype O, isolate 1 Manisa; 93Y=FMDV serotype O, isolate 1 Manisa VP2 S93Y; 93F=FMDV serotype O, isolate 1 Manisa VP2 S93F; 93W=FMDV serotype O, isolate 1 Manisa VP2 S93W; 97Q=FMDV serotype O, isolate 1 Manisa VP2 S97Q; 98F=FMDV serotype O, isolate 1 Manisa VP2 Y98F.

The invention claimed is:

1. A foot-and-mouth disease virus (FMDV) VP2 protein mutant, that comprises an amino acid substitution of a tyrosine at position number 93 (93Y), wherein the position number is relative to the numbering of the amino acids presented in SEQ ID NO: 1.

2. An FMDV capsid comprising the FMDV VP2 protein mutant of claim 1.

3. An isolated host cell comprising the FMDV VP2 protein mutant of claim 1.

4. A vaccine against FMD comprising a pharmaceutically acceptable carrier and an FMDV capsid comprising the FMDV VP2 protein mutant of claim 1.

5. An isolated host cell comprising the FMDV VP2 protein mutant of claim 1 and an FMDV capsid comprising said FMDV VP2 protein mutant.

6. A vaccine against FMD comprising a pharmaceutically acceptable carrier and the FMDV VP2 protein mutant of claim 1.

7. A vaccine against FMD comprising a pharmaceutically acceptable carrier and an isolated host cell comprising the FMDV VP2 protein mutant of claim 1.

8. A vaccine against FMD comprising a pharmaceutically acceptable carrier and one or more of the following: a foot-and-mouth disease virus (FMDV) VP2 protein mutant that comprises an amino acid substitution of a tyrosine at position number 93 (93Y), an FMDV capsid comprising said FMDV VP2 protein mutant, and an isolated host cell comprising said FMDV VP2 protein mutant;

wherein the position number is relative to the numbering of the amino acids presented in SEQ ID NO: 1.

9. A method for the vaccination against FMD of an animal susceptible for FMDV, comprising the step of inoculating the animal with the vaccine of claim 8.

* * * * *

SEQUENCE LISTING

```
<160> NUMBER OF SEQ ID NOS: 9

<210> SEQ ID NO 1
<211> LENGTH: 218
<212> TYPE: PRT
<213> ORGANISM: Foot-and-mouth disease virus

<400> SEQUENCE: 1

Asp Lys Lys Thr Glu Glu Thr Thr Leu Leu Glu Asp Arg Ile Leu Thr
1               5                   10                  15

Thr Arg Asn Gly His Thr Thr Ser Thr Thr Gln Ser Ser Val Gly Val
            20                  25                  30

Thr Tyr Gly Tyr Ala Thr Ala Glu Asp Phe Val Ser Gly Pro Asn Thr
        35                  40                  45

Ser Gly Leu Glu Thr Arg Val Val Gln Ala Glu Arg Phe Phe Lys Thr
    50                  55                  60

His Leu Phe Asp Trp Val Thr Ser Asp Ser Phe Gly Arg Cys His Leu
65                  70                  75                  80

Leu Glu Leu Pro Thr Asp His Lys Gly Val Tyr Gly Ser Leu Thr Asp
                85                  90                  95

Ser Tyr Ala Tyr Met Arg Asn Gly Trp Asp Val Glu Val Thr Ala Val
            100                 105                 110

Gly Asn Gln Phe Asn Gly Gly Cys Leu Leu Val Ala Met Val Pro Glu
        115                 120                 125

Leu Cys Ser Ile Gln Lys Arg Glu Leu Tyr Gln Leu Thr Leu Phe Pro
    130                 135                 140

His Gln Phe Ile Asn Pro Arg Thr Asn Met Thr Ala His Ile Thr Val
145                 150                 155                 160

Pro Phe Val Gly Val Asn Arg Tyr Asp Gln Tyr Lys Val His Lys Pro
                165                 170                 175

Trp Thr Leu Val Val Met Val Val Ala Pro Leu Thr Val Asn Thr Glu
            180                 185                 190

Gly Ala Pro Gln Ile Lys Val Tyr Ala Asn Ile Ala Pro Thr Asn Val
        195                 200                 205

His Val Ala Gly Glu Phe Pro Ser Lys Glu
    210                 215

<210> SEQ ID NO 2
<211> LENGTH: 12
<212> TYPE: PRT
<213> ORGANISM: Foot-and-mouth disease virus
```

```
<400> SEQUENCE: 2

His Lys Gly Val Tyr Gly Ser Leu Thr Asp Ser Tyr
1               5                   10

<210> SEQ ID NO 3
<211> LENGTH: 12
<212> TYPE: PRT
<213> ORGANISM: Foot-and-mouth disease virus

<400> SEQUENCE: 3

His Lys Gly Val Tyr Gly Ser Leu Thr Asp Ser Tyr
1               5                   10

<210> SEQ ID NO 4
<211> LENGTH: 12
<212> TYPE: PRT
<213> ORGANISM: Foot-and-mouth disease virus

<400> SEQUENCE: 4

Pro Lys Gly Val Tyr Gly Gly Leu Val Lys Ser Tyr
1               5                   10

<210> SEQ ID NO 5
<211> LENGTH: 12
<212> TYPE: PRT
<213> ORGANISM: Foot-and-mouth disease virus

<400> SEQUENCE: 5

His Lys Gly Val Tyr Gly Gly Leu Met Ala Ser Tyr
1               5                   10

<210> SEQ ID NO 6
<211> LENGTH: 12
<212> TYPE: PRT
<213> ORGANISM: Foot-and-mouth disease virus

<400> SEQUENCE: 6

His Lys Gly Val Tyr Gly His Leu Val Asp Ser Phe
1               5                   10

<210> SEQ ID NO 7
<211> LENGTH: 12
<212> TYPE: PRT
<213> ORGANISM: Foot-and-mouth disease virus

<400> SEQUENCE: 7

His Lys Gly Ile Tyr Gly Gln Leu Val Asp Ser His
1               5                   10

<210> SEQ ID NO 8
<211> LENGTH: 12
<212> TYPE: PRT
<213> ORGANISM: Foot-and-mouth disease virus

<400> SEQUENCE: 8

His Lys Gly Ile Tyr Gly Ser Leu Thr Asp Ala Tyr
1               5                   10
```

```
<210> SEQ ID NO 9
<211> LENGTH: 12
<212> TYPE: PRT
<213> ORGANISM: Foot-and-mouth disease virus

<400> SEQUENCE: 9

His Lys Gly Ile Tyr Gly Ala Met Leu Asp Ser His
1               5                   10
```